United States Patent
Amarasingham et al.

(10) Patent No.: US 10,755,369 B2
(45) Date of Patent: Aug. 25, 2020

(54) CLIENT MANAGEMENT TOOL SYSTEM AND METHOD

(71) Applicant: Parkland Center for Clinical Innovation, Dallas, TX (US)

(72) Inventors: Rubendran Amarasingham, Dallas, TX (US); Jennifer Wilson, Dallas, TX (US); Alexander Townes, Dallas, TX (US); Anand Shah, Dallas, TX (US); Stephanie Fenniri, Dallas, TX (US); Vaidyanatha Siva, Plano, TX (US)

(73) Assignee: Parkland Center for Clinical Innovation, Dallas, TX (US)

(*) Notice: Subject to any disclaimer, the term of this patent is extended or adjusted under 35 U.S.C. 154(b) by 665 days.

(21) Appl. No.: 14/798,630

(22) Filed: Jul. 14, 2015

(65) Prior Publication Data
US 2016/0019666 A1    Jan. 21, 2016

Related U.S. Application Data

(63) Continuation-in-part of application No. 14/682,836, filed on Apr. 9, 2015.
(Continued)

(51) Int. Cl.
*G06N 5/02* (2006.01)
*G06Q 50/24* (2012.01)
(Continued)

(52) U.S. Cl.
CPC .............. *G06Q 50/24* (2013.01); *G06N 5/04* (2013.01); *G16H 10/20* (2018.01); *G16H 10/60* (2018.01);
(Continued)

(58) Field of Classification Search
None
See application file for complete search history.

(56) References Cited

U.S. PATENT DOCUMENTS

| 3,225,179 A | 12/1965 | Harold et al. |
| 5,583,758 A | 12/1996 | McIlroy et al. |

(Continued)

FOREIGN PATENT DOCUMENTS

| WO | 2013033655 A1 | 3/2013 |
| WO | 2014042942 A1 | 3/2014 |
| WO | 2014105752 A1 | 7/2014 |

OTHER PUBLICATIONS

Knutson, et al., Predictive Modeling: A Guide for State Medicaid Purchasers, Center for Health Care Strategies, Inc., Aug. 2009, pp. 1-38.*

(Continued)

*Primary Examiner* — Wilbert L Starks
(74) *Attorney, Agent, or Firm* — Wei Wei Jeang; Grable Martin Fulton PLLC

(57) ABSTRACT

A client management tool system comprises a gateway module configured to provide access to a data store storing clinical and non-clinical data, a collection of computerized question forms configured to obtain additional data about a client, a social data model defining a structure to store and organize the client data, a predictive model including a plurality of weighted variables and thresholds in consideration of the client data to identify needs of the client and a valuation of services to address the client needs, a knowledgebase of available programs and service providers able to deliver the needed services, a client management toolkit configured to provide recommended a course of action in response to the identified client need, valuation, and available programs and services providers, and a data presenta- (Continued)

tion module operable to present notifications, alerts, and outcome report related to service delivery to the client.

20 Claims, 19 Drawing Sheets

Related U.S. Application Data

(60) Provisional application No. 62/025,063, filed on Jul. 16, 2014.

(51) Int. Cl.
*G06N 5/04* (2006.01)
*G16H 10/20* (2018.01)
*G16H 10/60* (2018.01)
*G16H 40/20* (2018.01)
*G16H 50/30* (2018.01)
*G16H 50/50* (2018.01)
*G16H 50/70* (2018.01)
*G16H 50/20* (2018.01)

(52) U.S. Cl.
CPC ............ *G16H 40/20* (2018.01); *G16H 50/30* (2018.01); *G16H 50/50* (2018.01); *G06N 5/02* (2013.01); *G16H 50/20* (2018.01); *G16H 50/70* (2018.01)

(56) References Cited

U.S. PATENT DOCUMENTS

| | | | |
|---|---|---|---|
| 5,950,214 A | 9/1999 | Rivette et al. |
| 6,288,646 B1 | 9/2001 | Skardon |
| 6,826,540 B1 | 11/2004 | Plantec et al. |
| 7,395,216 B2 | 7/2008 | Rosenfeld et al. |
| 7,490,085 B2 | 2/2009 | Walker et al. |
| 7,617,078 B2 | 11/2009 | Rao et al. |
| 8,241,642 B2 | 8/2012 | Zagursky et al. |
| 8,293,489 B2 | 10/2012 | Henkin |
| 8,489,414 B2 | 7/2013 | McEachern |
| 8,506,934 B2 | 8/2013 | Henkin |
| 8,515,777 B1 | 8/2013 | Rajasenan |
| 8,595,159 B2 | 11/2013 | McNair |
| 8,663,938 B2 | 3/2014 | Henkin |
| 8,682,696 B1 | 3/2014 | Shanmugam |
| 8,859,004 B2 | 10/2014 | Zhang et al. |
| 8,968,706 B2 | 3/2015 | Henkin |
| 9,147,041 B2 | 9/2015 | Amarasingham et al. |
| 2002/0116222 A1 | 8/2002 | Wurster |
| 2002/0152096 A1 | 10/2002 | Falchuk et al. |
| 2002/0169584 A1 | 11/2002 | Fu et al. |
| 2003/0101076 A1 | 5/2003 | Zaleski |
| 2004/0122706 A1 | 6/2004 | Walker et al. |
| 2004/0122708 A1 | 6/2004 | Avinash et al. |
| 2004/0242972 A1 | 12/2004 | Adak et al. |
| 2005/0191716 A1 | 9/2005 | Surwit et al. |
| 2005/0197982 A1 | 9/2005 | Saidi et al. |
| 2005/0203773 A1 | 9/2005 | Soto et al. |
| 2006/0031101 A1 | 2/2006 | Ross |
| 2006/0036619 A1 | 2/2006 | Fuerst et al. |
| 2006/0129427 A1 | 6/2006 | Wennberg |
| 2006/0184489 A1 | 8/2006 | Weiner et al. |
| 2006/0271408 A1 | 11/2006 | Rosenfeld |
| 2007/0021981 A1 | 1/2007 | Cox |
| 2007/0073559 A1 | 3/2007 | Stangel |
| 2007/0094048 A1 | 4/2007 | Grichnik |
| 2007/0118399 A1 | 5/2007 | Avinash et al. |
| 2007/0156456 A1 | 7/2007 | McGillin et al. |
| 2007/0198296 A1 | 8/2007 | Pellinat et al. |
| 2007/0255586 A1 | 11/2007 | Green et al. |
| 2007/0288266 A1 | 12/2007 | Sysko et al. |
| 2008/0010254 A1 | 1/2008 | Settimi |
| 2008/0106374 A1 | 5/2008 | Sharbaugh |
| 2008/0146277 A1 | 6/2008 | Anglin et al. |
| 2008/0164998 A1 | 7/2008 | Scherpbier et al. |
| 2008/0186137 A1 | 8/2008 | Butler et al. |
| 2008/0235049 A1 | 9/2008 | Morita et al. |
| 2008/0240425 A1 | 10/2008 | Rosales et al. |
| 2008/0275738 A1 | 11/2008 | Shillingburg |
| 2008/0306763 A1 | 12/2008 | James |
| 2009/0048866 A1 | 2/2009 | Mahesh et al. |
| 2009/0106692 A1 | 4/2009 | Bhavani |
| 2009/0164236 A1 | 6/2009 | Gounares et al. |
| 2009/0164248 A1 | 6/2009 | Hunt et al. |
| 2009/0240525 A1 | 9/2009 | Sadler et al. |
| 2009/0281838 A1 | 11/2009 | Lynn et al. |
| 2010/0001838 A1 | 1/2010 | Miodownik et al. |
| 2010/0017225 A1 | 1/2010 | Oakley et al. |
| 2010/0083164 A1 | 4/2010 | Martin et al. |
| 2010/0094648 A1 | 4/2010 | Seward |
| 2010/0114588 A1 | 5/2010 | Moitra et al. |
| 2010/0131434 A1 | 5/2010 | Magent et al. |
| 2010/0153270 A1 | 6/2010 | Hawkes |
| 2010/0177659 A1 | 7/2010 | Hethuin et al. |
| 2010/0189236 A1 | 7/2010 | MacDonald |
| 2010/0249531 A1 | 9/2010 | Hanlon et al. |
| 2010/0280847 A1 | 11/2010 | Schaffer |
| 2011/0009760 A1 | 1/2011 | Zhang et al. |
| 2011/0077973 A1 | 3/2011 | Breitenstein et al. |
| 2011/0093288 A1 | 4/2011 | Soto et al. |
| 2011/0099487 A1 | 4/2011 | Pyhalammi et al. |
| 2011/0145018 A1 | 6/2011 | Fotsch et al. |
| 2011/0145041 A1 | 6/2011 | Salamatov et al. |
| 2011/0184250 A1 | 7/2011 | Schmidt et al. |
| 2011/0202486 A1 | 8/2011 | Fung et al. |
| 2011/0218253 A1 | 9/2011 | Lange et al. |
| 2011/0225114 A1 | 9/2011 | Gotthardt |
| 2011/0295621 A1 | 12/2011 | Farooq et al. |
| 2012/0046965 A1 | 2/2012 | Ryan et al. |
| 2012/0056720 A1 | 3/2012 | Barvick et al. |
| 2012/0060216 A1 | 3/2012 | Chaudhri et al. |
| 2012/0078661 A1 | 3/2012 | Sheldon et al. |
| 2012/0084092 A1 | 4/2012 | Kozuch et al. |
| 2012/0095352 A1 | 4/2012 | Tran |
| 2012/0101846 A1 | 4/2012 | Gotthardt et al. |
| 2012/0112883 A1 | 5/2012 | Wallace et al. |
| 2012/0179479 A1 | 7/2012 | Waterson et al. |
| 2012/0185267 A1 | 7/2012 | Kamen et al. |
| 2012/0191476 A1 | 7/2012 | Reid et al. |
| 2012/0231959 A1 | 9/2012 | Elton et al. |
| 2012/0245464 A1 | 9/2012 | Tran |
| 2012/0251993 A1 | 10/2012 | Chidambaran et al. |
| 2012/0296671 A1 | 11/2012 | Simons-Nikolova et al. |
| 2013/0013333 A1 | 1/2013 | Gopinathan et al. |
| 2013/0034589 A1 | 2/2013 | Zhang et al. |
| 2013/0047113 A1 | 2/2013 | Hume et al. |
| 2013/0095459 A1 | 4/2013 | Tran |
| 2013/0096939 A1 | 4/2013 | Russell |
| 2013/0185097 A1 | 7/2013 | Sada et al. |
| 2013/0262357 A1 | 10/2013 | Amarasingham et al. |
| 2013/0304498 A1 | 11/2013 | Rangadass |
| 2013/0317844 A1 | 11/2013 | Hammond et al. |
| 2013/0318027 A1 | 11/2013 | Almogy et al. |
| 2014/0074509 A1 | 3/2014 | Amarasingham et al. |
| 2014/0095201 A1 | 4/2014 | Farooq et al. |
| 2014/0095420 A1 | 4/2014 | Chun et al. |
| 2014/0221765 A1 | 8/2014 | Harmon et al. |
| 2014/0249855 A1 | 9/2014 | Moore |
| 2014/0304200 A1 | 10/2014 | Wall |
| 2014/0350954 A1 | 11/2014 | Ellis et al. |
| 2015/0025329 A1 | 1/2015 | Amarasingham et al. |
| 2015/0025909 A1 | 1/2015 | Hayter |
| 2015/0066539 A1 | 3/2015 | Sheffer et al. |
| 2015/0106123 A1 | 4/2015 | Amarasingham et al. |
| 2015/0242586 A1 | 8/2015 | Kagen |
| 2016/0110523 A1 | 4/2016 | Francois |
| 2016/0203281 A1 | 7/2016 | Zalis et al. |
| 2016/0314256 A1 | 10/2016 | Su et al. |

OTHER PUBLICATIONS

Knutson, et al., Predictive Modeling: A Guide for State Medicaid Purchasers, Center for Health Care Strategies, Inc., Aug. 2009, pp. 1-38 (Year: 2009).*

(56) References Cited

OTHER PUBLICATIONS

Escudero, J., et al., "Early Detection and Characterization of Alzheimer's Disease in Clinical Scenarios Using Bioprofile Concepts and K-Means," 33rd Annual International Conference of the IEEE EMBS, Aug. 30-Sep. 3, 2011, pp. 6470-6473.

Festersen, P.L., et al., "Re: Mind: A mobile application for bipolar disorder patients," Wireless Mobile Communication and Healthcare (Mobihealth), Nov. 3-5, 2014, pp. 343-346.

International Search Report and Written Opinion received in corresponding Patent Cooperation Treaty Application No. PCT/US2013/058159, dated Dec. 19, 2013, 8 pages.

International Search Report and Written Opinion received in corresponding Patent Cooperation Treaty Application No. PCT/US2015/025200, dated Jul. 20, 2015, 8 pages.

International Search Report and Written Opinion received in corresponding Patent Cooperation Treaty Application No. PCT/US2015/025202, dated Jul. 16, 2015, 9 pages.

International Search Report and Written Opinion received in corresponding Patent Cooperation Treaty Application No. PCT/US2015/025203, dated Jul. 28, 2015, 9 pages.

International Search Report and Written Opinion received in corresponding Patent Cooperation Treaty Application No. PCT/US2015/025207, dated Jul. 28, 2015, 11 pages.

International Search Report and Written Opinion received in corresponding Patent Cooperation Treaty Application No. PCT/US2015/025205, dated Jul. 28, 2015, 8 pages.

International Search Report and Written Opinion received in corresponding Patent Cooperation Treaty Application No. PCT/US2015/025206, dated Jul. 16, 2015, 7 pages.

Lorincz, K., et al., "Wearable Wireless Sensor Network to Assess Clinical Status in Patients with Neurological Disorders," Information Processing in Sensor Networks, Apr. 25-27, 2007, pp. 563-564.

Moorman, J. R., et al., "Predictive monitoring for early detection of subacute potentially catastrophic illnesses in critical care," 33rd Annual International Conference of the IEEE EMBS, Aug. 30-Sep. 3, 2011, pp. 5515-5518.

Alvarez, Carlos A., et al., "Predicting Out of Intensive Care Unit Cardiopulmonary Arrest or Death Using Electronic Medical Record Data," BMC Medical Informatics and Decision Making, Feb. 27, 2013, 11 pages.

Amarasingham, Ruben, et al., "Allocating Scarce Resources in Real-Time to Reduce Heart Failure Readmissions: A Prospective, Controlled Study," BMJ Quality and Safety Online First, Jul. 31, 2013, 10 pages.

Amarasingham, Ruben, et al., "An Automated Model to Identify Heart Failure Patients at Risk for 30-Day Readmission or Death Using Electronic Medical Record Data," Medical Care, vol. 48, No. 11, Nov. 2010, pp. 981-988.

Amarasingham, Ruben, et al., "Clinical Information Technology Capabilities in Four U.S. Hospitals, Testing a New Structural Performance Measure," Medical Care, vol. 44, No. 3, Mar. 2006, pp. 216-224.

Amarasingham, Ruben, et al., "Clinical Information Technologies and Inpatient Outcomes, A Multiple Hospital Study," Arch Intern Med, vol. 169, No. 2, Jan. 26, 2009, pp. 108-114.

Amarasingham, Ruben, et al., "Electronic Medical Record-Based Multicondition Models to Predict the Risk of 30 Day Readmission or Death Among Adult Medicine Patients: Validation and Comparison to Existing Models," BMC Medical Informatics and Decision Making, May 20, 2015, 8 pages.

Amarasingham, Ruben, et al., "Implementing Electronic Health Care Predictive Analytics: Considerations and Challengtes," Health Affairs, 33, No. 7, Jul. 2014, pp. 1148-1154.

Amarasingham, Ruben, et al., "A Rapid Admission Protocol to Reduce Emergency Department Boarding Times," BMJ Quality and Safety Online First, Feb. 8, 2010, pp. 200-204.

Bates, David W., et al., "Big Data in Health Care: Using Analytics to Identify and Manage High-Risk and High-Cost Patients," Health Affairs, 33, No. 7, Jul. 2014, pp. 1123-1131.

Bates, David W., "The Effects of Health Information Technology on Inpatient Care," Arch Intern Med, vol. 169, No. 2, Jan. 26, 2009, pp. 105-107.

Cohen, Glenn, et al., "The Legal and Ethical Concerns that Arise from Using Complex Predictive Analytics in Health Care,", Health Affairs, 33, No. 7, Jul. 2014, pp. 1139-1147.

Kansagara, Devan, et al., "Risk Prediction Models for Hospital Readmission, A Systematic Review," JAMA, vol. 306, No. 15, Oct. 19, 2011, pp. 1688-1698.

Makam, Anil N., et al., "Identifying Patients with Diabetes and the Earliest Data of Diagnosis in Real Time: An Electronic Health Record Case-Finding Algorithm," BMC Medical Informatics and Decision Making, Aug. 1, 2013, 7 pages.

McAlister, Finlay A., "Decreasing Readmissions: It Can Be Done But One Size Does Not Fit All," BMJ Quality and Safety Online First, Sep. 4, 2013, 3 pages.

Nehra, Mahendra S., et al., "Use of Administrative Claims Data for Identifying Patients with Cirrhosis," J Clin Gastroenterol, vol. 47, No. 5, May/Jun. 2013, pp. e50-e54.

Nijhawan, Ank E., "An Electronic Medical Record-Based Model to Predict 30-Day Risk of Readmission and Death Among HIV-Infected Inpatients," J Acquir Immune Defic Syndr, vol. 61, No. 3, Nov. 1, 2012, pp. 349-358.

Ram, Sudha, et al., "Predicting Asthma-Related Emergency Department Visits Using Big Data," IEEE Journal of Biomedical and Health Informatics, vol. 19, No. 4, Jul. 2015, pp. 1216-1223.

Singal, A.G., et al., "An Automated Model Using Electronic Medical Record Data Identifies Patients with Cirrhosis at High Risk for Readmission," Clinical Gastroenterology and Hepatology, vol. 11, No. 10, Oct. 2013, pp. 1335-1341.

Allen, Arthur, "The Frequent Flier" Program That Grounded a Hospital's Soaring Costs, www.politico.com, Dec. 18, 2017.

Baeza-Yates, Ricardo, et al, "Modem Informational Retrieval", ACM Press Books, 1999.

Baxt, William G., A Neural Computational Aid to the Diagnosis of Acute Myocardial Infarction, Annals of Emergency Medicine 39.4, Apr. 2002, pp. 366-373.

Birge, John R., et al., "Using Fuzzy Neural Network to Solve Short-Term Load Forecasting Problems", Dept. of Industrial & Operations Engineering, University of Michigan, Technical Report 96-20, 1996.

European Search Report received in European Application No. 13837780.9, dated Mar. 23, 2016.

European Search Report received in European Application No. 14827115.8, dated Feb. 21, 2017.

European Search Report received in European Application No. 14854100.6, dated May 18, 2017.

European Search Report received in European Application No. 15776758.3, dated Dec. 6. 2017.

European Search Report received in European Application No. 15777433.2, dated Jan. 2, 2018.

European Search Report received in European Application No. 15777472.0, dated Dec. 6, 2017.

European Search Report received in European Application No. 15777492.8, dated Dec. 11, 2017.

European Search Report received in European Application No. 15822510.2, dated Jun. 11, 2018.

European Search Report received in European Application No. 16858162.7, dated Jan. 18, 2019.

Healthit, Clinical Decision Support: More Than Just Alerts Tipsheet, Jul. 2015.

International Search Report and Written Opinion received in Patent Cooperation Treaty Application No. PCT/US2014/046029, dated Nov. 13, 2014.

International Search Report and Written Opinion received in Patent Cooperation Treaty Application No. PCT/US2014/060496, dated Feb. 3, 2015.

International Search Report and Written Opinion received in Patent Cooperation Treaty Application No. PCT/US2015/040335, dated Sep. 30, 2015.

International Search Report and Written Opinion received in Patent Cooperation Treaty Application No. PCT/US2016/048796, dated Nov. 29, 2016.

(56) References Cited

OTHER PUBLICATIONS

International Search Report and Written Opinion received in Patent Cooperation Treaty Application No. PCT/US2016/057773, dated Jan. 12, 2017.
Liu, Hai, et al., "Integration of RFID and Wireless Sensor Networks", Chapter 13, 1st Reading, Aug. 14, 2008.
Maran, Alberto, "Continuous Subcutaneous Glucose Monitoring in Diabetic Patients," Diabetes Care, vol. 25, No. 2, Feb. 2002, pp. 347-352.
Stockman, "Communication by Means of Reflected Power", Proceedings of the IRE, Oct. 1948, pp. 1196-1204.
Wikipedia, "Computer-Assisted Personal Interviewing", Mar. 31, 2018.

* cited by examiner

CLIENT MANAGEMENT TOOL SYSTEM AND METHOD

RELATED APPLICATION

The present disclosure claims the benefit of U.S. Provisional Patent Application, Ser. No. 62/025,063, filed on Jul. 16, 2014, and is a Continuation-In-Part Application of Holistic Hospital Patient Care and Management System and Method for Automated Patient Monitoring, Ser. No. 14/682,836, filed on Apr. 9, 2015, all of which are incorporated herein by reference.

FIELD

The present disclosure relates to a client management tool system and method. In particular, the present disclosure relates to the design of a technologically advanced client management and client tracking tool equipped with highly configurable features with analytics and the ability to calibrate those analytics.

BACKGROUND

A major challenge facing Community-based service organizations today is the ability to track outcomes and the impact of programs and services in the community. In the climate of shrinking funding for social programs, the need to assess program effectiveness and monitor and track outcomes to demonstrate value to grantors, donors, and ultimately attract more funding to support an organization's mission has never been greater.

Additionally, due to resource constraints, individual organizations simply are unable to maintain and support an IT group for the longer-term.

Lastly, case workers and volunteers who are largely non-technical simply do not want to use a cumbersome and non-intuitive system. Case workers require flexible workflows in order to deliver effortless client management, and often times, these case workers resort to using paper forms to document and plan and track client status and needs. If client management and client tracking is not executed electronically, real-time electronic exchange of useful client information is hindered, preventing the organization from achieving efficiencies around client service delivery.

BRIEF DESCRIPTION OF THE DRAWINGS

FIG. 10-20 are exemplary screenshots of a client management tool system and method according to the present disclosure.

DETAILED DESCRIPTION

The client management tool described herein delivers a decision support function that provides a holistic view of clients and facilitates the review of social and clinical factors for case planning. It is personalized for the end-user therefore resulting in superior service with the ability to report pertinent outcomes and facilitate program evaluation. End users can range from Program Directors to Case Managers to Volunteers and anyone who interface with clients in a meaningful way. Also, the built-in reports allow for continuous evaluation of programs and client management efforts.

Figure 1:
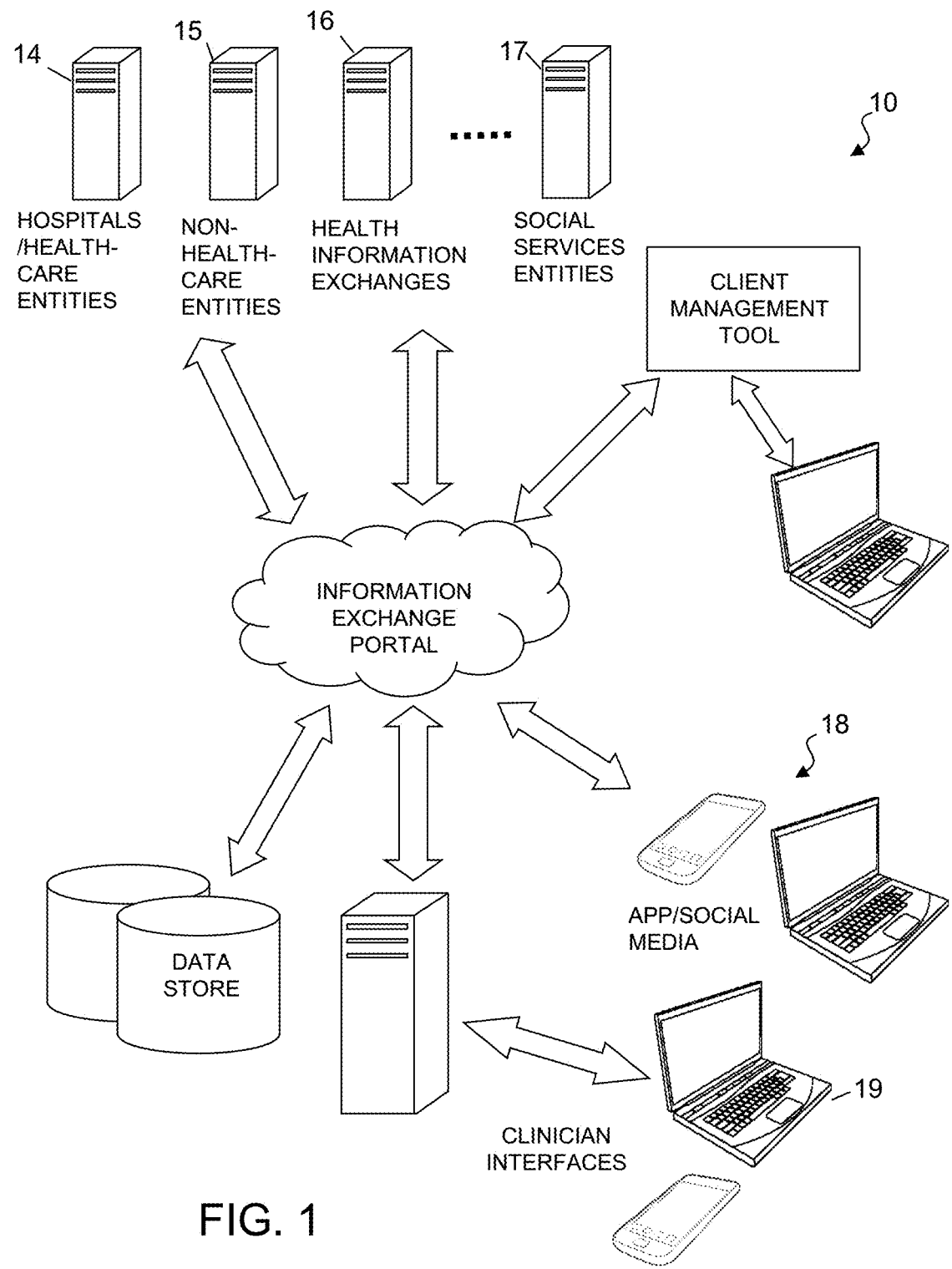
FIG. 1 is a simplified block diagram of an exemplary embodiment of a client management tool system and method according to the present disclosure.

FIG. 1 is a simplified block diagram of an exemplary embodiment of a client management tool system and method 10 according to the present disclosure. Case managers are at the front line, meeting with clients to help them navigate vast array of programs and services as well as internal offerings. The client management tool system and method 10 can increase the case manager's productivity and ensure efficiency and flexibility in the workflow. The client management tool system 10 includes a computer system (hardware and software) adapted to receive a variety of clinical and non-clinical data relating to patients or individuals requiring care, education, therapy, and client management. The variety of data include real-time data streams and historical or stored data from hospitals and healthcare entities 14, non-health care entities 15, health information exchanges 16, and social-to-health information exchanges and social services entities 17, for example. These data are used by the client management tool system and method 10 to determine a Relative Value Unit (RVU) for clients of community-based service organizations so that they may receive more personalized and coordinated care that are better suited to their particular condition and needs. The RVU enables a quantification or valuation of service delivery. It should be noted that the computer system may comprise one or more local or remote computer servers operable to transmit data and communicate via wired and wireless communication links and computer networks.

The client management tool system 10 may have access to data that include electronic medical records (EMR) that include both clinical and non-clinical data. The EMR clinical data may be received from entities such as hospitals, clinics, pharmacies, laboratories, and health information exchanges, including: vital signs and other physiological data; data associated with comprehensive or focused history and physical exams by a physician, nurse, or allied health professional; medical history; prior allergy and adverse medical reactions; family medical history; prior surgical history; emergency room records; medication administration records; culture results; dictated clinical notes and records; gynecological and obstetric history; mental status examination; vaccination records; radiological imaging exams; invasive visualization procedures; psychiatric treatment history; prior histological specimens; laboratory data; genetic information; physician's notes; networked devices and monitors (such as blood pressure devices and glucose meters); pharmaceutical and supplement intake information; and focused genotype testing.

The EMR non-clinical data may include, for example, social, behavioral, lifestyle, and economic data; type and nature of employment; job history; medical insurance information; hospital utilization patterns; exercise information; addictive substance use; occupational chemical exposure; frequency of physician or health system contact; location and frequency of habitation changes; predictive screening health questionnaires such as the patient health questionnaire (PHQ); personality tests; census and demographic data; neighborhood environments; diet; gender; marital status; education; proximity and number of family or care-giving assistants; address; housing status; social media data; and educational level. The non-clinical patient data may further include data entered by the patients, such as data entered or uploaded to a social media website.

Additional sources or devices of EMR data may provide, for example, lab results, medication assignments and changes, EKG results, radiology notes, daily weight readings, and daily blood sugar testing results. These data sources may be from different areas of the hospital, clinics, patient care facilities, patient home monitoring devices, among other available clinical or healthcare sources.

As shown in FIG. 1, patient data sources may include non-healthcare entities 15. These are entities or organizations that are not thought of as traditional healthcare providers. These entities 15 may provide non-clinical data that include, for example, gender; marital status; education; community and religious organizational involvement; proximity and number of family or care-giving assistants; address; census tract location and census reported socioeconomic data for the tract; housing status; number of housing address changes; frequency of housing address changes; requirements for governmental living assistance; ability to make and keep medical appointments; independence on activities of daily living; hours of seeking medical assistance; location of seeking medical services; sensory impairments; cognitive impairments; mobility impairments; educational level; employment; and economic status in absolute and relative terms to the local and national distributions of income; climate data; and health registries. Such data sources may provide further insightful information about patient lifestyle, such as the number of family members, relationship status, individuals who might help care for a patient, and health and lifestyle preferences that could influence health outcomes.

The client management tool system and method 10 according to the present disclosure. The client management tool system 10 may further receive data from an information exchange portal (IEP). The IEP is one of a group of Health Information Exchanges (HIE). The Health Information Exchanges are organizations that mobilize healthcare information electronically across organizations within a region, community or hospital system. HIEs are increasingly developed to share clinical and non-clinical patient data between healthcare entities within cities, states, regions, or within umbrella health systems. Data may arise from numerous sources such as hospitals, clinics, consumers, payers, physicians, labs, outpatient pharmacies, ambulatory centers, nursing homes, and state or public health agencies.

A subset of HIEs connect healthcare entities to community organizations that do not specifically provide health services, such as non-governmental charitable organizations, social service agencies, and city agencies. The clinical predictive and monitoring system 10 may receive data from these social services organizations and social-to-health information exchanges 17, which may include, for example, information on daily living skills, availability of transportation to doctor appointments, employment assistance, training, substance abuse rehabilitation, counseling or detoxification, rent and utilities assistance, homeless status and receipt of services, medical follow-up, mental health services, meals and nutrition, food pantry services, housing assistance, temporary shelter, home health visits, domestic violence, appointment adherence, discharge instructions, prescriptions, medication instructions, neighborhood status, and ability to track referrals and appointments.

Another source of data include social media or social network services 18, such as FACEBOOK, GOOGLE+, and other websites. Such information sources 18 (represented by, but are not limited to, mobile phones and laptop computers) can provide information such as the number of family members, relationship status, identify individuals who may help care for a patient, and health and lifestyle preferences that may influence health outcomes. These social media data may be received from the websites, with the individual's permission, and some data may come directly from a user's computing devices (mobile phones, tablet computers, laptops, etc.) as the user enters status updates, for example.

The system 10 may further receive input and data from a number of additional sources, such as devices that are used to track and monitor the clients. For example, RFID (Radio Frequency Identification) tags may be worn, associated with, or affixed to patients during a hospital stay and after discharge. Another source of location data may include Global Position System (GPS) data from a clinician's or patient's mobile telephones or other devices. The GPS coordinates may be received from the mobile devices and used to pinpoint a person's location if RFID data is not available. Using GPS data, a patient may be tracked and monitored during clinical visits, social services appointments, and visits and appointments with other care providers. The patient's location information may be used to monitor and predict patient utilization patterns of clinical services (e.g., emergency department, urgent care clinic, specialty clinic), social service organizations (e.g., food pantries, homeless shelters, counseling services), and the frequency of use of these services. These data may be used for analysis by the predictive model of the system.

These non-clinical patient data may potentially provide a much more realistic and accurate depiction of the patient's overall holistic healthcare environment. Augmented with such non-clinical patient data, the analysis and predictive modeling performed by the present system to identify patients at high-risk of readmission or disease recurrence become much more robust and accurate.

The client management tool system and method 10 are accessible from or are configured to operate on a variety of computing devices (mobile devices, tablet computers, laptop computers, desktop computers, servers, etc.). These computing devices are equipped to display a graphical user interface to present data and reports, input data, and configure the client management tool system and method described in more detail below.

As shown in FIG. 1, the client management tool system and method 10 may receive data streamed real-time, or from historic or batched data from various data sources. The real-time and stored data may be in a wide variety of formats according to a variety of protocols, including CCD, XDS, HL7, SSO, HTTPS, EDI, CSV, etc. The data may be encrypted or otherwise secured in a suitable manner. The data may be pulled (polled) by the system 10 from the various data sources or the data may be pushed to the system 10 by the data sources. Alternatively or in addition, the data may be received in batch processing according to a predetermined schedule or on-demand. The client management tool system and method 10 may include one or more local databases, servers, memory, drives, and other suitable storage devices. Alternatively or in addition, the data may be stored in a data center in the cloud.

The client management tool system and method 10 include a computer system that may comprise a number of computing devices, including servers, that may be located locally or in a cloud computing farm. The data paths between the computer system and the databases may be encrypted or otherwise protected with security measures or transport protocols now known or later developed.

Figure 2:
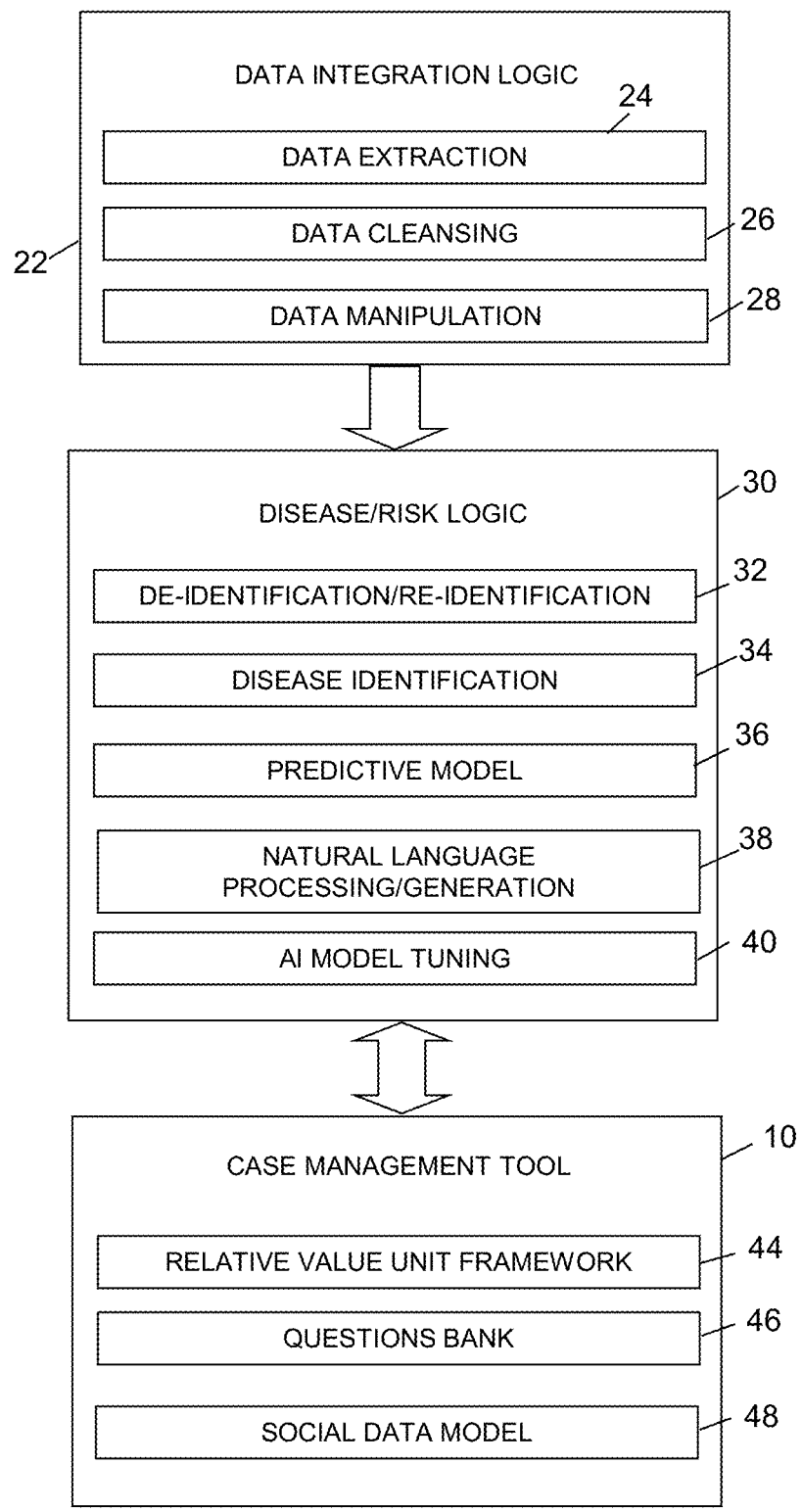
FIG. 2 is a simplified logical block diagram of an exemplary embodiment of a clinical predictive and monitoring system and method according to the present disclosure.

FIG. 2 is a simplified logical block diagram of an exemplary embodiment of a clinical predictive and monitoring system and method according to the present disclosure. Because the system and method 10 receive and extract data from many disparate sources in myriad formats pursuant to different protocols, the incoming data must first undergo a multi-step process before they may be properly analyzed and utilized. A data integration logic module 22 further includes a data extraction process 24, a data cleansing process 26, and a data manipulation process 28. It should be noted that although the data integration logic module 22 is shown to have distinct processes 24-28, these are done for illustrative purposes only and these processes may be performed in parallel, iteratively, and interactively.

The data extraction process 24 extracts clinical and non-clinical data from data sources in real-time or in historical batch files either directly or through the Internet, using various technologies and protocols. Preferably in real-time, the data cleansing process 26 "cleans" or pre-processes the data, putting structured data in a standardized format and preparing unstructured text for natural language processing (NLP) to be performed in the disease/risk logic module 30 described below. The system may also receive "clean" data and convert them into desired formats (e.g., text date field converted to numeric for calculation purposes).

The data manipulation process 28 may analyze the representation of a particular data feed against a meta-data dictionary and determine if a particular data feed should be re-configured or replaced by alternative data feeds. For example, a given hospital EMR may store the concept of "maximum creatinine" in different ways. The data manipulation process 28 may make inferences in order to determine which particular data feed from the EMR would best represent the concept of "creatinine" as defined in the meta-data dictionary and whether a feed would need particular re-configuration to arrive at the maximum value (e.g., select highest value).

The data integration logic module 22 then passes the pre-processed data to a disease/risk logic module 30. The disease risk logic module 30 is operable to calculate a risk score associated with an identified disease or condition for each patient and identifying those patients who should receive targeted intervention and care. The disease/risk logic module 30 includes a de-identification/re-identification process 32 that is adapted to remove all protected health information according to HIPAA standards before the data is transmitted over the Internet. It is also adapted to re-identify the data. Protected health information that may be removed and added back may include, for example, name, phone number, facsimile number, email address, social security number, medical record number, health plan beneficiary number, account number, certificate or license number, vehicle number, device number, URL, all geographical subdivisions smaller than a State, including street address, city, county, precinct, zip code, and their equivalent geocodes (except for the initial three digits of a zip code, if according to the current publicly available data from the Bureau of the Census), Internet Protocol number, biometric data, and any other unique identifying number, characteristic, or code.

The disease/risk logic module 30 further includes a disease identification process 34. The disease identification process 34 is adapted to identify one or more diseases or conditions of interest for each patient. The disease identification process 34 considers data such as lab orders, lab values, clinical text and narrative notes, and other clinical and historical information to determine the probability that a patient has a particular disease. Additionally, during disease identification, natural language processing is conducted on unstructured clinical and non-clinical data to determine the disease or diseases that the physician believes are prevalent. This process 34 may be performed iteratively over the course of many days to establish a higher confidence in the disease identification as the physician becomes more confident in the diagnosis. New or updated patient data may not support a previously identified disease, and the system would automatically remove the patient from that disease list. The natural language processing combines a rule-based model and a statistically-based learning model.

The disease identification process 34 utilizes a hybrid model of natural language processing, which combines a rule-based model and a statistically-based learning model. During natural language processing, raw unstructured data, for example, physicians' notes and reports, first go through a process called tokenization. The tokenization process divides the text into basic units of information in the form of single words or short phrases by using defined separators such as punctuation marks, spaces, or capitalizations. Using the rule-based model, these basic units of information are identified in a meta-data dictionary and assessed according to predefined rules that determine meaning Using the statistical-based learning model, the disease identification process 34 quantifies the relationship and frequency of word and phrase patterns and then processes them using statistical algorithms. Using machine learning, the statistical-based learning model develops inferences based on repeated patterns and relationships. The disease identification process 34 performs a number of complex natural language processing functions including text pre-processing, lexical analysis, syntactic parsing, semantic analysis, handling multi-word expression, word sense disambiguation, and other functions.

For example, if a physician's notes include the following: "55 yo m c h/o dm, cri. now with adib rvr, chfexac, and rle cellulitis going to 10 W, tele." The data integration logic 22 is operable to translate these notes as: "Fifty-five-year-old male with history of diabetes mellitus, chronic renal insufficiency now with atrial fibrillation with rapid ventricular response, congestive heart failure exacerbation and right lower extremity cellulitis going to 10 West and on continuous cardiac monitoring."

Continuing with the prior example, the disease identification process 34 is adapted to further ascertain the following: 1) the patient is being admitted specifically for atrial fibrillation and congestive heart failure; 2) the atrial fibrillation is severe because rapid ventricular rate is present; 3) the cellulitis is on the right lower extremity; 4) the patient is on continuous cardiac monitoring or telemetry; and 5) the patient appears to have diabetes and chronic renal insufficiency.

The disease/risk logic module 30 further comprises a predictive model process 36 that is adapted to predict the risk of particular diseases or condition of interest according to one or more predictive models. For example, if the hospital desires to determine the level of risk for future readmission for all patients currently admitted with heart failure, the heart failure predictive model may be selected for processing patient data. However, if the hospital desires to determine the risk levels for all internal medicine patients for any cause, an all-cause readmissions predictive model may be used to process the patient data. As another example, if the hospital desires to identify those patients at risk for short-term and long-term diabetic complications, the diabetes predictive model may be used to target those patients. Other predictive models may include HIV readmission, diabetes identification, risk for cardio-pulmonary arrest, kidney disease progression, acute coronary syndrome, pneumonia, cirrhosis, all-cause disease-independent readmission, colon cancer pathway adherence, and others.

Continuing to use the prior example, the predictive model for congestive heart failure may take into account a set of risk factors or variables, including the worst values for laboratory and vital sign variables such as: albumin, total bilirubin, creatine kinase, creatinine, sodium, blood urea nitrogen, partial pressure of carbon dioxide, white blood cell count, troponin-I, glucose, internationalized normalized ratio, brain natriuretic peptide, pH, temperature, pulse, diastolic blood pressure, and systolic blood pressure. Further, non-clinical factors are also considered, for example, the number of home address changes in the prior year, risky health behaviors (e.g., use of illicit drugs or substance), number of emergency room visits in the prior year, history of depression or anxiety, and other factors. The predictive model specifies how to categorize and weight each variable or risk factor, and the method of calculating the predicted probably of readmission or risk score. In this manner, the clinical predictive and monitoring system and method 10 is able to stratify, in real-time, the risk of each patient that arrives at a hospital or another healthcare facility. Therefore, those patients at the highest risks are automatically identified so that targeted intervention and care may be instituted. One output from the disease/risk logic module 30 includes the risk scores of all the patients for particular disease or condition. In addition, the module 30 may rank the patients according to the risk scores, and provide the identities of those patients at the top of the list. For example, the hospital may desire to identify the top 20 patients most at risk for congestive heart failure readmission, and the top 5% of patients most at risk for cardio-pulmonary arrest in the next 24 hours. Other diseases and conditions that may be identified using predictive modeling include, for example, HIV readmission, diabetes identification, kidney disease progression, colorectal cancer continuum screening, meningitis management, acid-base management, anticoagulation management, etc.

The disease/risk logic module 30 may further include a natural language processing & generation module 38. The natural language generation module 38 is adapted to receive the output from the predictive model 36 such as the risk score and risk variables for a patient, and "translate" the data to present the evidence that the patient is at high-risk for that disease or condition. This module 30 thus provides the intervention coordination team additional information that supports why the patient has been identified as high-risk for the particular disease or condition. In this manner, the intervention coordination team may better formulate the targeted inpatient and outpatient intervention and treatment plan to address the patient's specific situation.

The disease/risk logic module 30 further includes an artificial intelligence (AI) model tuning process 40. The artificial intelligence model tuning process 38 utilizes adaptive self-learning capabilities using machine learning technologies. The capacity for self-reconfiguration enables the system and method 10 to be sufficiently flexible and adaptable to detect and incorporate trends or differences in the underlying patient data or population that may affect the predictive accuracy of a given algorithm. The artificial intelligence model tuning process 40 may periodically retrain a selected predictive model for improved accurate outcome to allow for selection of the most accurate statistical methodology, variable count, variable selection, interaction terms, weights, and intercept for a local health system or clinic. The artificial intelligence model tuning process 40 may automatically modify or improve a predictive model in three exemplary ways. First, it may adjust the predictive weights of clinical and non-clinical variables without human supervision. Second, it may adjust the threshold values of specific variables without human supervision. Third, the artificial intelligence model tuning process 40 may, without human supervision, evaluate new variables present in the data feed but not used in the predictive model, which may result in improved accuracy. The artificial intelligence model tuning process 40 may compare the actual observed outcome of the event to the predicted outcome then separately analyze the variables within the model that contributed to the incorrect outcome. It may then re-weigh the variables that contributed to this incorrect outcome, so that in the next reiteration those variables are less likely to contribute to a false prediction. In this manner, the artificial intelligence model tuning process 40 is adapted to reconfigure or adjust the predictive model based on the specific clinical setting or population in which it is applied. Further, no manual reconfiguration or modification of the predictive model is necessary. The artificial intelligence model tuning process 40 may also be useful to scale the predictive model to different health systems, populations, and geographical areas in a rapid timeframe.

As an example of how the artificial intelligence model tuning process 40 functions, the sodium variable coefficients may be periodically reassessed to determine or recognize that the relative weight of an abnormal sodium laboratory result on a new population should be changed from 0.1 to 0.12. Over time, the artificial intelligence model tuning process 38 examines whether thresholds for sodium should be updated. It may determine that in order for the threshold level for an abnormal sodium laboratory result to be predictive for readmission, it should be changed from, for example, 140 to 136 mg/dL. Finally, the artificial intelligence model tuning process 40 is adapted to examine whether the predictor set (the list of variables and variable interactions) should be updated to reflect a change in patient population and clinical practice. For example, the sodium variable may be replaced by the NT-por-BNP protein variable, which was not previously considered by the predictive model.

The client management tool system and method 10 work with and utilize data from the disease/risk logic module 30. The client management tool system and method 10 include three main components: a Relative Value Unit (RVU) framework 44, a questions bank 46, and social data models 48.

The RVU framework 44 is a comprehensive framework for calculating the Relative Value Units (RVUs) or a value for the services or programs targeted at specific conditions of a client. The RVU provides a way to measure and quantify the "degree of difficulty" associated with a specific case. The RVU framework 44 uses artificial intelligence and other tools to evaluate the individual's contributing factors, such as those factors that influence a person's health status, including social, environmental factors, clinical factors, etc. The RVU framework 44 also takes into account the individual's health condition and severity or significance of any diseases, and the type of care, services, and programs the individual will need to achieve improved outcomes. For example, taking care of a terminally sick, homeless senior with an addiction problem is arguably more complicated and challenging than providing temporary services for someone who is in between jobs. The comprehensive, extensible, intelligent solution that is claimed as novel enables, through a combination of artificial intelligence and business rules on a big data platform, a quantification of the "degree of difficulty" and the "value" associated with the particular case by determining an associated RVU score for the client's case.

The questions bank 46 is a super set of questions that may be posed to a client at intake or during the visit. These questions are related to a client-centric extensible social data model 48, which defines how the answers to the questions or data should be organized and structured. The data in the data model are assigned RVUs.

Figure 3:
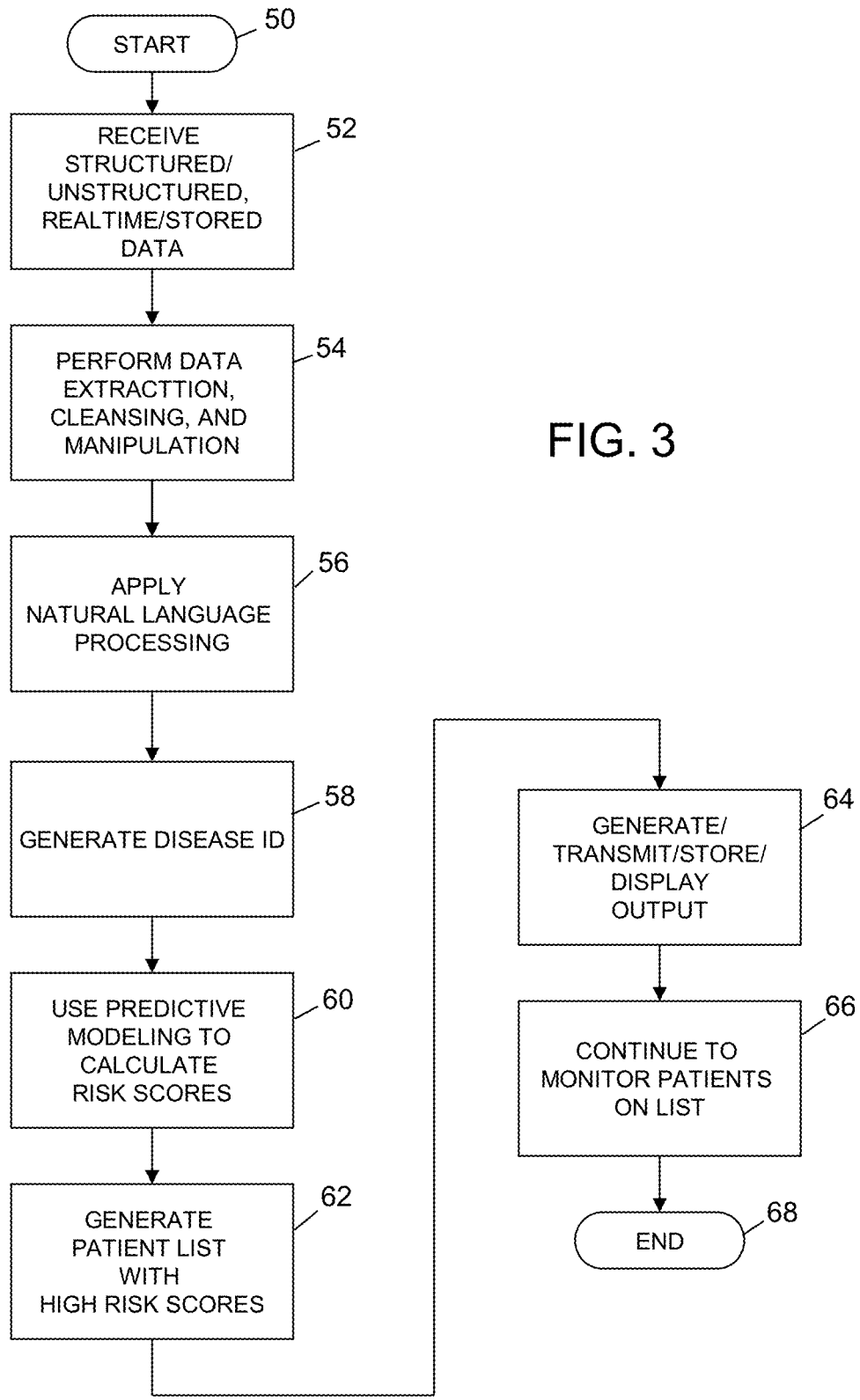
FIG. 3 is a simplified flowchart of an exemplary embodiment of a clinical predictive model 50 according to the present disclosure.

FIG. 3 is a simplified flowchart of an exemplary embodiment of a clinical predictive model 50 according to the present disclosure. The predictive modeling method 50 receives structured and unstructured clinical and non-clinical data related to specific patients from a variety of sources and in a number of different formats, as shown in block 52. These data may be encrypted or protected using data security methods now known or later developed. In block 54, the method 50 pre-processes the received data, such as data extraction, data cleansing, and data manipulation. Other data processing techniques now known and later developed may be utilized. In block 56, data processing methods such as natural language processing and other suitable techniques may be used to translate or otherwise make sense of the data. In block 58, by analyzing the pre-processed data, one or more diseases or conditions of interest as related to each patient are identified. In block 60, the method 50 applies one or more predictive models to further analyze the data and calculate one or more risk scores for each patient as related to the identified diseases or conditions. In blocks 62 and 64, one or more lists showing those patients with the highest risks for each identified disease or condition are generated, transmitted, and otherwise presented to medical staff, such as members of an intervention coordination team. These lists may be generated on a daily basis or according to another desired schedule. The intervention coordination team may then prescribe and follow targeted intervention and treatment plans for inpatient and outpatient care. In block 66, those patients identified as high-risk are continually monitored while they are undergoing inpatient and outpatient care. The method 50 ends in block 68.

Not shown explicitly in FIG. 3 is the de-identification process, in which the data become disassociated with the patient's identity to comply with HIPAA regulations. The data can be de-coupled with the patient's identity whenever they are transmitted over wired or wireless network links that may be compromised, and otherwise required by HIPAA. The method 50 is further adapted to reunite the patient data with the patient's identity.

Figure 4:
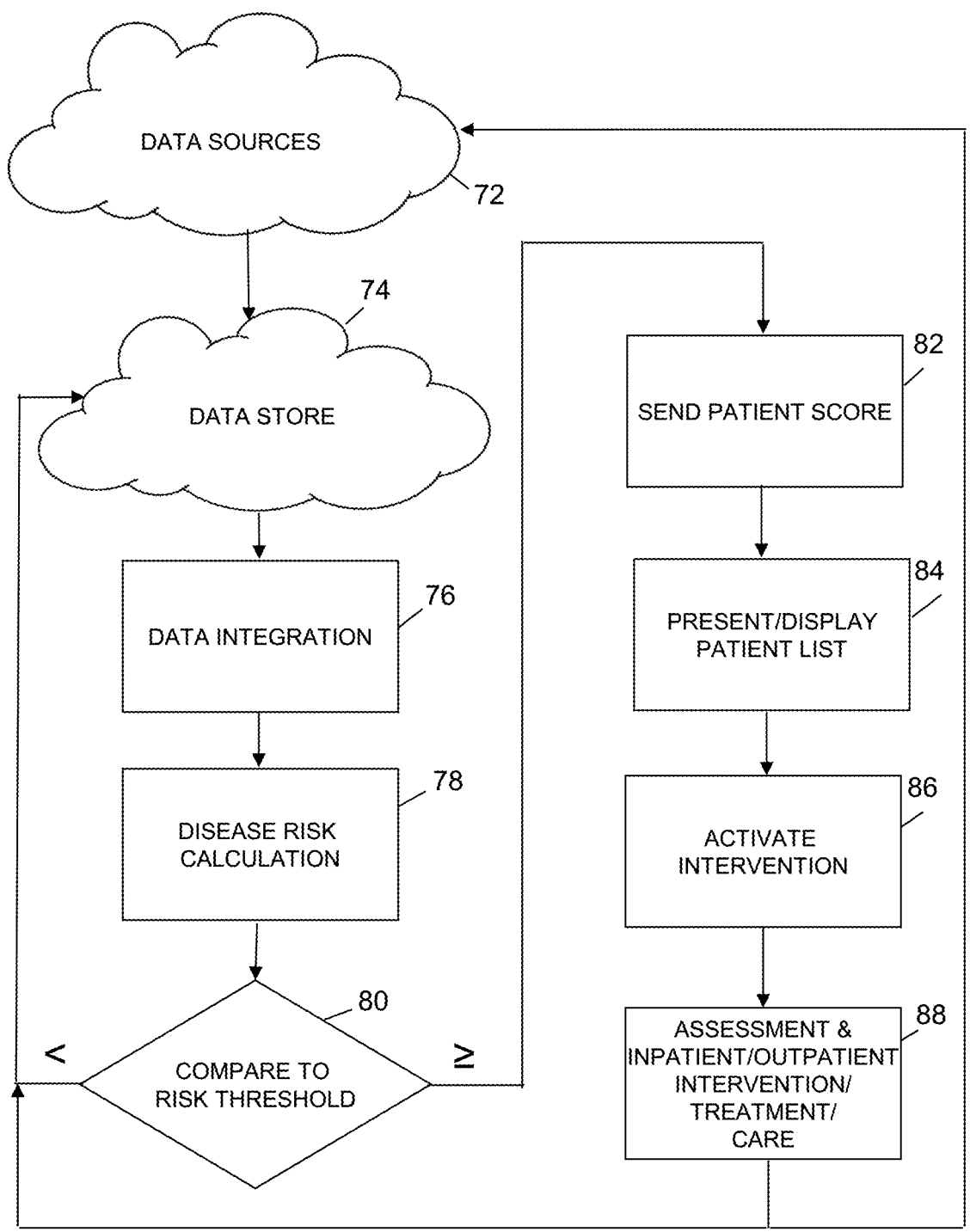
FIG. 4 is a simplified flowchart/block diagram of an exemplary embodiment of a clinical predictive modeling method 50 according to the present disclosure.

FIG. 4 is a simplified flowchart/block diagram of an exemplary embodiment of a clinical predictive modeling method 50 according to the present disclosure. A variety of data are received from a number of disparate data sources 72 related to particular patients admitted at a hospital or a healthcare facility. The incoming data may be received in real-time or the data may be stored as historical data received in batches or on-demand. The incoming data are stored in a data store 74. In block 76, the received data undergo a data integration process (data extraction, data cleansing, data manipulation), as described above. The resultant pre-processed data then undergoes the disease logic process 78 during which de-identification, disease identification, and predictive modeling are performed. The risk score computed for each patient for a disease of interest or an adverse event is compared to a disease risk threshold in block 80. Each disease is associated with its own risk threshold. If the risk score is less than the risk threshold, then the process returns to data integration and is repeated when new data associated with a patient become available. If the risk score is greater than or equal to the risk threshold, then the identified patient having the high risk score is included in a patient list in block 82. In block 84, the patient list and other associated information may then be presented to the intervention coordination team in one or more possible ways, such as transmission to and display on a desktop or mobile device in the form of a text message, e-mail message, web page, etc. In this manner, an intervention coordination team is notified and activated to target the patients identified in the patient list for assessment, and inpatient and outpatient treatment and care, as shown in block 88. The process may thereafter provide feedback data to the data sources 72 and/or return to data integration 86 that continues to monitor the patient during his/her targeted inpatient and outpatient intervention and treatment. Data related to the patient generated during the inpatient and outpatient care, such as prescribed medicines and further laboratory results, radiological images, etc. is continually monitored according to pre-specified algorithms which define the patient/client's care plan, including post-discharge social services and programs.

Figure 5:
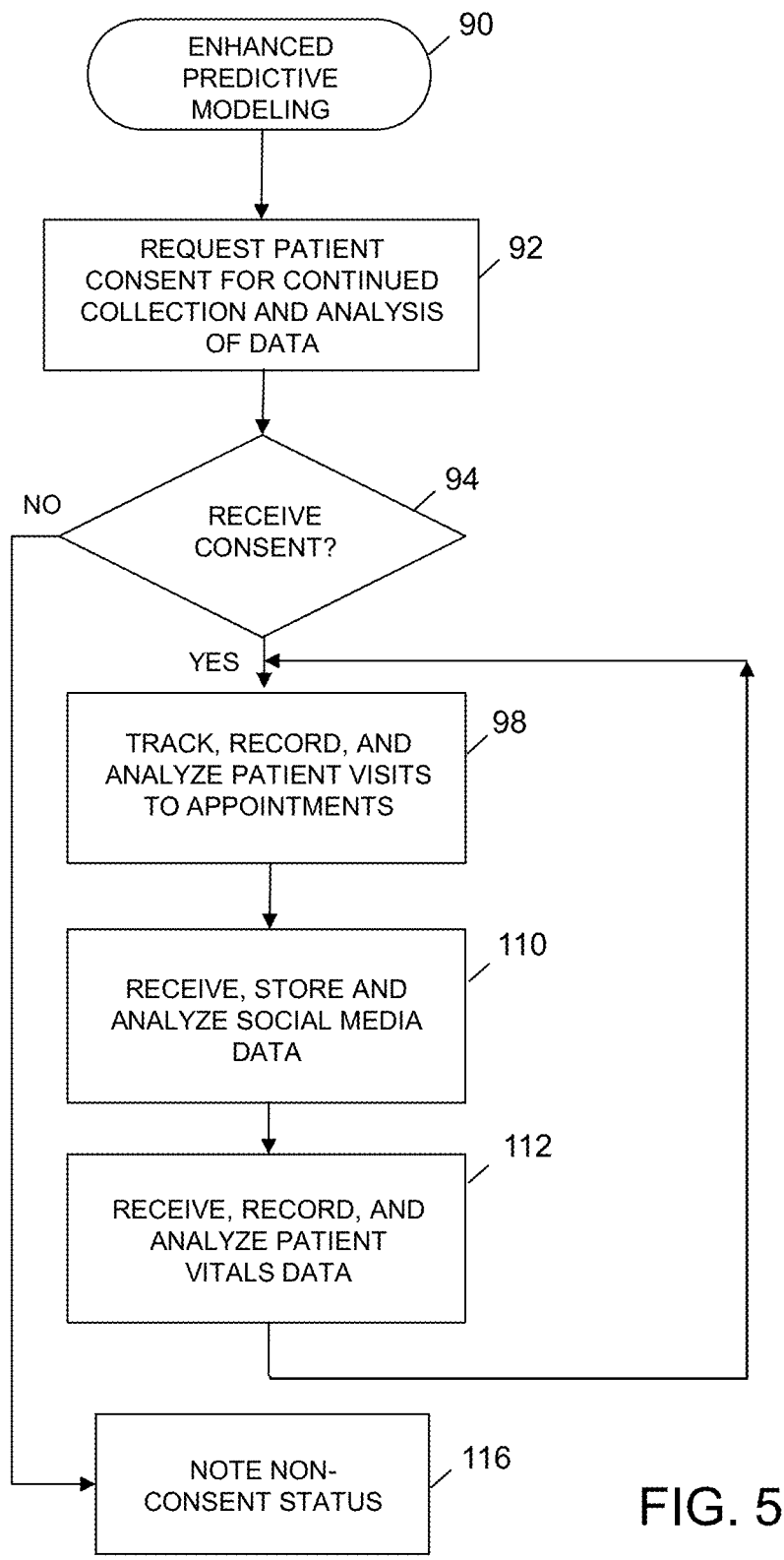
FIG. 5 is a simplified flowchart of an exemplary embodiment of an enhanced predictive modeling method 90 according to the present disclosure.

FIG. 5 is a simplified flowchart of an exemplary embodiment of an enhanced predictive modeling method 90 according to the present disclosure. In block 92, the patient's consent for continued collection and analysis of the patient's data is requested. Because the enhanced method will continue to track and monitor the patient's wellbeing and collect data associated with the patient or client for analysis, the patient's consent is sought to comply with all local, state, and federal requirements. If the patient's consent is not received or the patient declined, as determined in block 94, then the patient's no consent status is recorded in the system's database, as shown in block 96. If the consent is received in block 94, then the patient's visits to clinical/medical and non-medical/social appointments are monitored and tracked and data recorded, as shown in block 98. This may be done automatically, such as tracking the patient's location using, for example, RFID, WiFi, or GPS methods. Alternatively, data received or taken at each visit to these scheduled or unscheduled appointments are recorded in the system for analysis. The patient's social media data may also be received and stored for analysis, as shown in block 110. Further, the patient's vitals may be continuously monitored and taken automatically or otherwise for analysis, as shown in block 112. The patient may be wearing an electronic device that is capable of measuring the vitals of the patient on a periodic basis, such as once or twice a day. This information may be automatically relayed or transmitted to the system 10 directly or via a portal or information exchange. The enhanced predictive model is capable of serving as a reliable warning tool for the timely detection and prevention of patient adverse events. Its functionality may include patient risk stratification, notification of clinical staff of an adverse event, and identification of health service and social service utilization.

Figure 6:
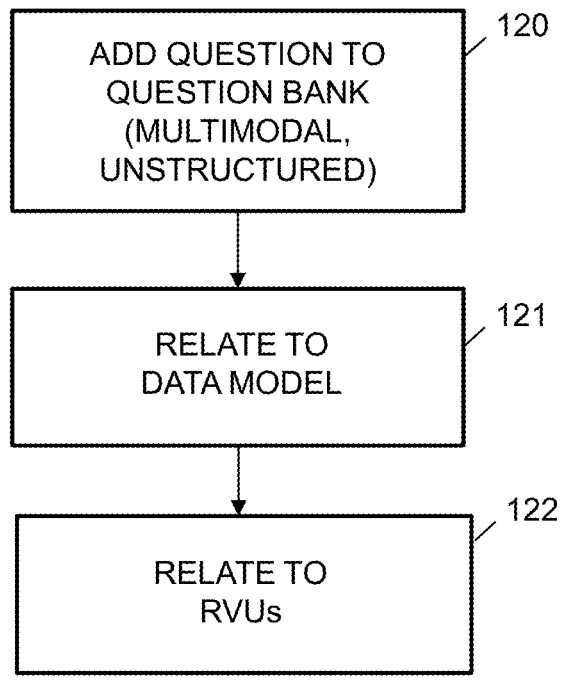
FIG. 6 is a simplified flowchart of an exemplary embodiment of a question bank configuration process for the client management tool system and method according to the present disclosure.

FIG. 6 is a simplified flowchart of an exemplary embodiment of a questions bank configuration process for the client management tool system and method 10 according to the present disclosure. A community-based service organization may input additional questions that will be posed to clients to supply more information to the questions bank, as shown in block 120. Each question is related to the social data model that will determine how an answer to the question will be evaluated and analyzed, as shown in block 121. The data is also assigned an RVU that is a value point system that can be used to quantify the care, condition, improvement, or progress of the client, as shown in block 122.

Figure 7:
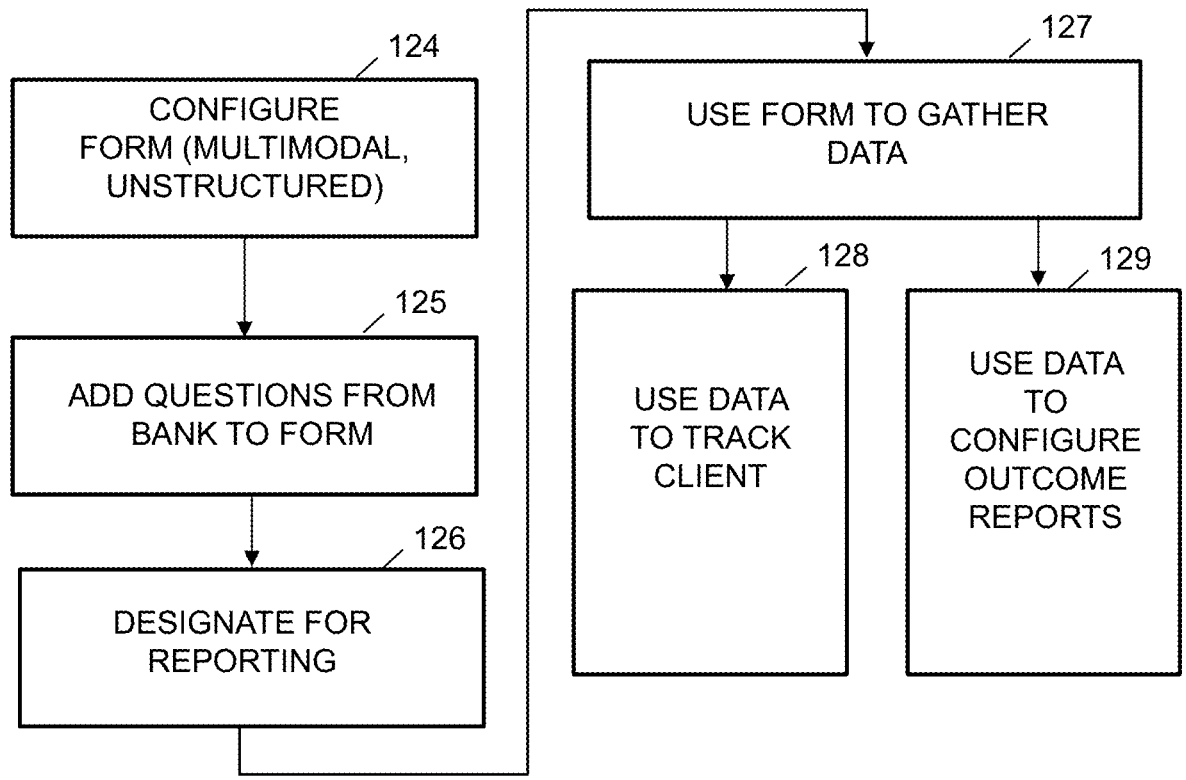
FIG. 7 is a simplified flowchart of an exemplary embodiment of a form configuration process for the client management tool system and method according to the present disclosure.

FIG. 7 is a simplified flowchart of an exemplary embodiment of a form configuration process 124 for the client management tool system and method 10 according to the present disclosure. The community-based service organization may configure question forms used at intake or during service delivery by selecting questions from the questions bank, as shown in block 125. The questions can also be selected to form the basis of customized reports or other forms of output, as shown in block 126. The configured forms are used to query the client and obtain data that are then input into the system 10, as shown in block 127. The client management tool system and method 10 then uses the data to track and monitor client progress, and to compose outcome reports, as shown in blocks 128 and 129. This output may be transmitted wirelessly or via LAN, WAN, the Internet, and delivered to healthcare facilities' electronic medical record stores, user electronic devices (e.g., pager, text messaging program, mobile telephone, tablet computer, mobile computer, laptop computer, desktop computer, and server), health information exchanges, and other data stores, databases, devices, and users.

Figure 8:
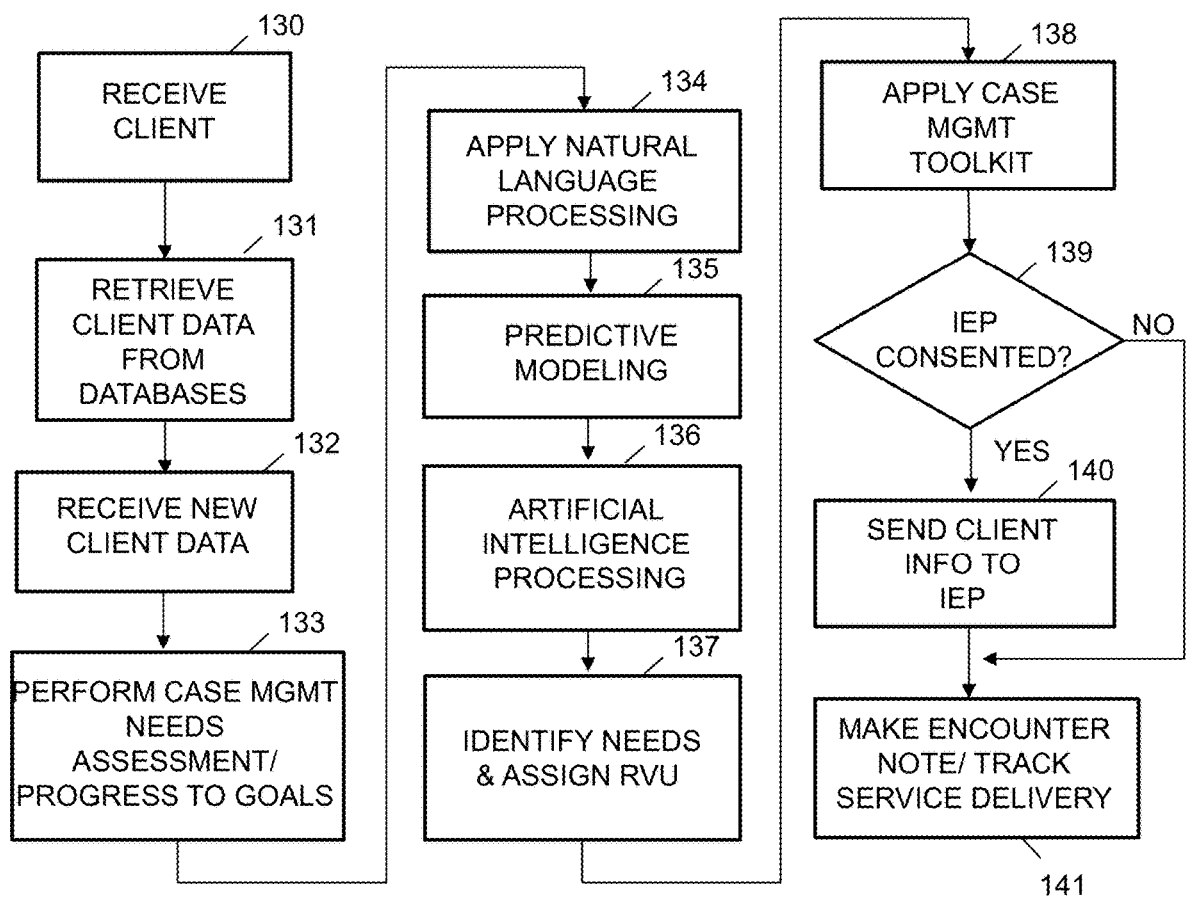
FIG. 8 is a simplified flowchart of an exemplary embodiment of a client management method according to the present disclosure.

FIG. 8 is a simplified flowchart of an exemplary embodiment of a client management method according to the present disclosure. The client comes into a community-based service organization and is greeted and received by a case manager, as shown in block 130. The case manager uses the client management tool system to retrieve data related to the client from local and/or remote databases, including obtaining data via the IEP, as shown in block 131. The case manager may additionally ask the client a series of questions including using one or more configured forms to obtain further information to enhance the understanding of the client's current condition and needs, as shown in block 132. The client management tool system then applies the data integration logic, predictive modeling, and artificial intelligence processing to analyze the data, as shown in blocks 133-136. The system then identify the needs of the client, and calculates and assigns a RVU score, as shown in block 137.

Based on the identified needs and the RVU, the system further selects and applies a client management toolkit that provides detailed information and recommendations for a customized client management plan that includes best practices of care for the client, as shown in block 138. A client management toolkit may include various forms, such as intake and assessment forms, that streamlines and facilitates the intake and assessment processes, for example. The toolkit may also include recommended and proven activities and services for a client with the identified needs. Organizations that are successful with certain types of cases may create toolkits that may be shared with other service providers in the community. If the client has consented to have his/her information accessed via the IEP, as determined in block 139, then the client information is transmitted to the IEP, as shown in block 140, otherwise, this step is skipped. The case manager may then input encounter notes and may also use the tool to track service delivery, as shown in block 141.

Figure 9:
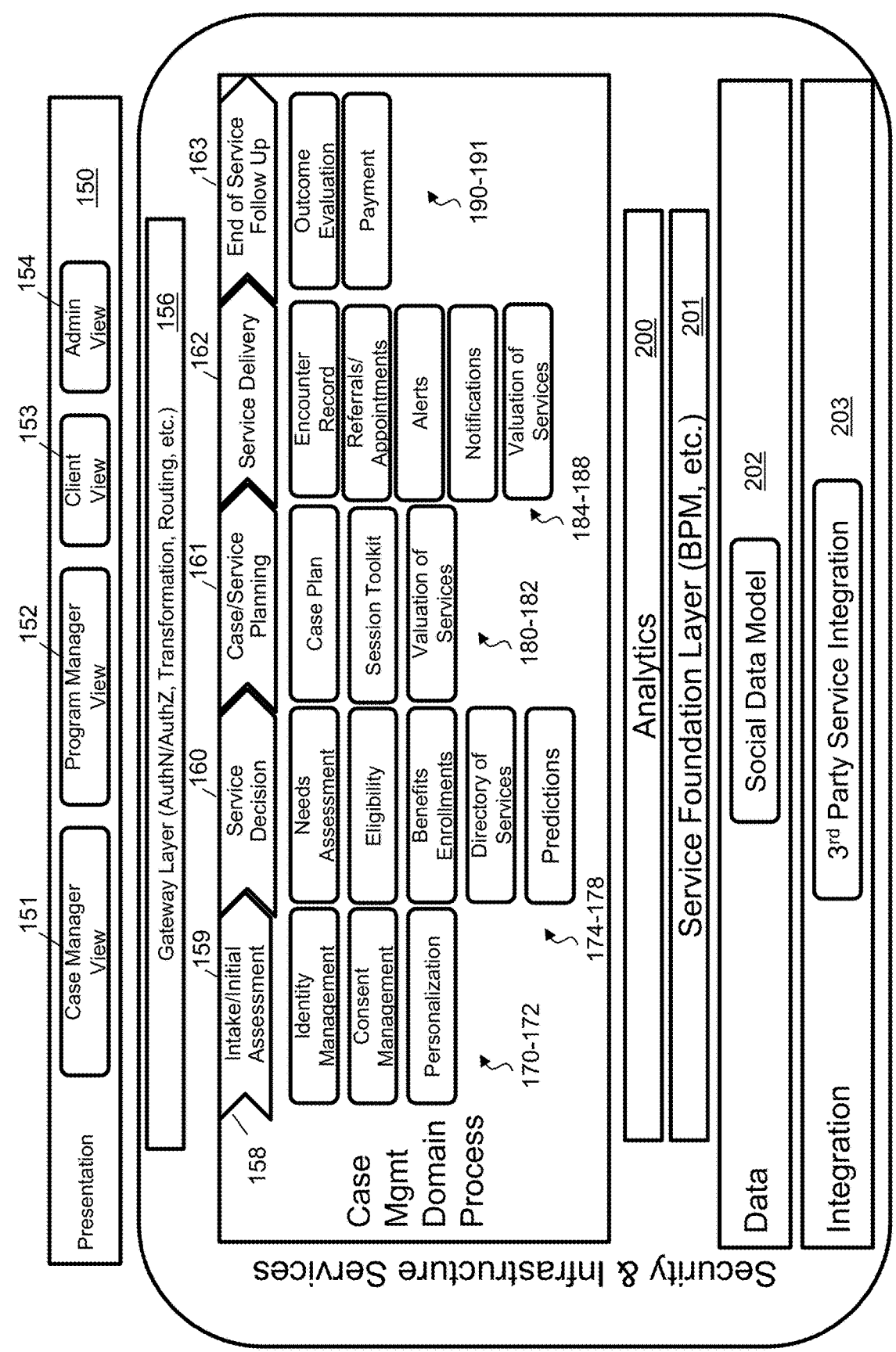
FIG. 9 is a simplified architectural diagram of an exemplary embodiment of a client management tool system and method 10 according to the present disclosure.

FIG. 9 is a simplified architectural diagram of an exemplary embodiment of a client management tool system and method 10 according to the present disclosure. The architecture diagram shows a role-based presentation layer 150 that includes a case manager view 151, program manager view 152, client view 153, and administrator view 154. A case manager is someone who interfaces and works directly with clients. A program manager oversees the case managers and are in charge of the program that clients are enrolled in. An administrator is someone who helps to set up each service organization and the users in the system and method. The administrator of the system may perform a number of operations with the system, such as provide configuration data for the organization and users to provide system access and authorization. The administrator may also generate new questions and formulate new forms by selecting questions from the questions bank. The administrator may also configure the client management toolkits, messaging preferences, and outcome reports.

The system architecture further includes a gateway layer 156 that performs routing, transmission, receiving, authentication, encryption, and decryption according to a variety of communication protocols now known or to be developed. The architecture further includes a client management work flow 158 that includes a number of stages: intake/initial assessment 159, service decision 160, case/service planning 161, service delivery 162, and end of service follow-up 163. These stages in the client management work flow are described in more detail below.

The intake/initial assessment stage 159 includes a number of client management processes: identity management 170, consent management 171, and personalization 172. The case manager may efficiently and effectively search and filter through the client list using a number of criteria (including client name, ID number, user role, etc.) to find records related to a particular client. The case manager may view existing client records and create a new client record in the system and update client information. The system further provides consent forms so that the client may agree and authorize access to his/her information. The case manager can also easily scan and upload required documents from the client.

The service decision stage 160 includes: needs assessment 174, eligibility 175, benefits enrollment 176, directory of services 177, and predictions 178. The case manager may use the system to set client-driven goals influenced by the organization's mission. The system may further suggest internal referrals across the organization as well as external referrals to partner organizations. The system also processes incoming referrals from within and outside the organization. The system may be used by the case manager to track referrals and referral history. The system further provides a searchable directory of services by category of service. The system further enables the case manager to assess eligibility and match to programs and services.

The case/service planning stage 161 includes: client management plan toolkit 180, session toolkit 181, and valuation of services 182. The system captures client-specific action items by providing the ability for the case manager to use "sticky note" messages, that include relevant client information and provide reminders. The client management plan toolkit is tailored to the client's needs and condition, and is customized for self-sufficiency education and planning. The toolkit includes recommendations of programs, services, as well as educational materials and/or classes on topics. The system also makes recommended client management activities and milestones, and further automates calendar integration for appointment scheduling. A valuation of services and programs recommended for the client is performed by calculating the RVU score.

The service delivery stage 162 includes: encounter record 184, referrals/appointments 185, alerts 186, notifications 187, and valuation of services 188. During this stage 162, the case manager may input case or encounter notes into the system. The system also tracks service delivery encounters, and makes/records appointments. The system is further integrated with the IEP so that updates and notifications about client information are exchanged, and the system has access to the most current client information on hospital stays, ER visits, doctor visits, and medications. A valuation of services and programs delivered to the client is performed by calculating the RVU score.

The end of service follow-up stage 163 includes: outcome evaluation 190 and payment 191. The system 10 may be used to conduct exit interviews with clients exiting the program. The client's record can be automatically put in inactive mode. Outcome reports may be obtained to summarize the client's data. Payment for the services and programs may be tied to the client achieving certain goals or requirements.

The client management work flow and processes 158 are built on analytics 200 and logic, which is support by a service foundation layer 201, social data model 202, and third party integration 203. The predictive analytics 200 uses real-time and historic data, along with surveillance data to predict the likelihood of an adverse event. The service foundation layer 201 includes core infrastructure services that address authentication, security, reporting etc. The social data model 202 includes a clinical data warehouse (CDW), which is a multitenant, immutable clinical data store and data warehouse for clinical and social data originating from public and private sources, including but not limited to medical records, social status, family information and organization data. It provides data extraction and data population services for both data entry, data sharing and analytical systems. CDW also has data tagging and historical audit capabilities. CDW allows linking of information across multiple tenant with both identified and de-identified information. Third party service integration 203 refers to a service for notification purposes that provides the means to integrate with third party services such as referral services, lookup services, etc.

FIG. 10-20 are exemplary screenshots of a client management tool system and method 10 according to the present disclosure. FIG. 10 shows a screenshot of an exemplary screen display that a case manager may view. On the left side of the screen is a list of clients under the care of the case manager 210, and on the right side of the screen is her client management calendar 212. The case manager may highlight or click on any date and the appointments for the selected date would be displayed. The appointment details may include the client's name, which may be linked to the client's detailed information.

Figure 11:
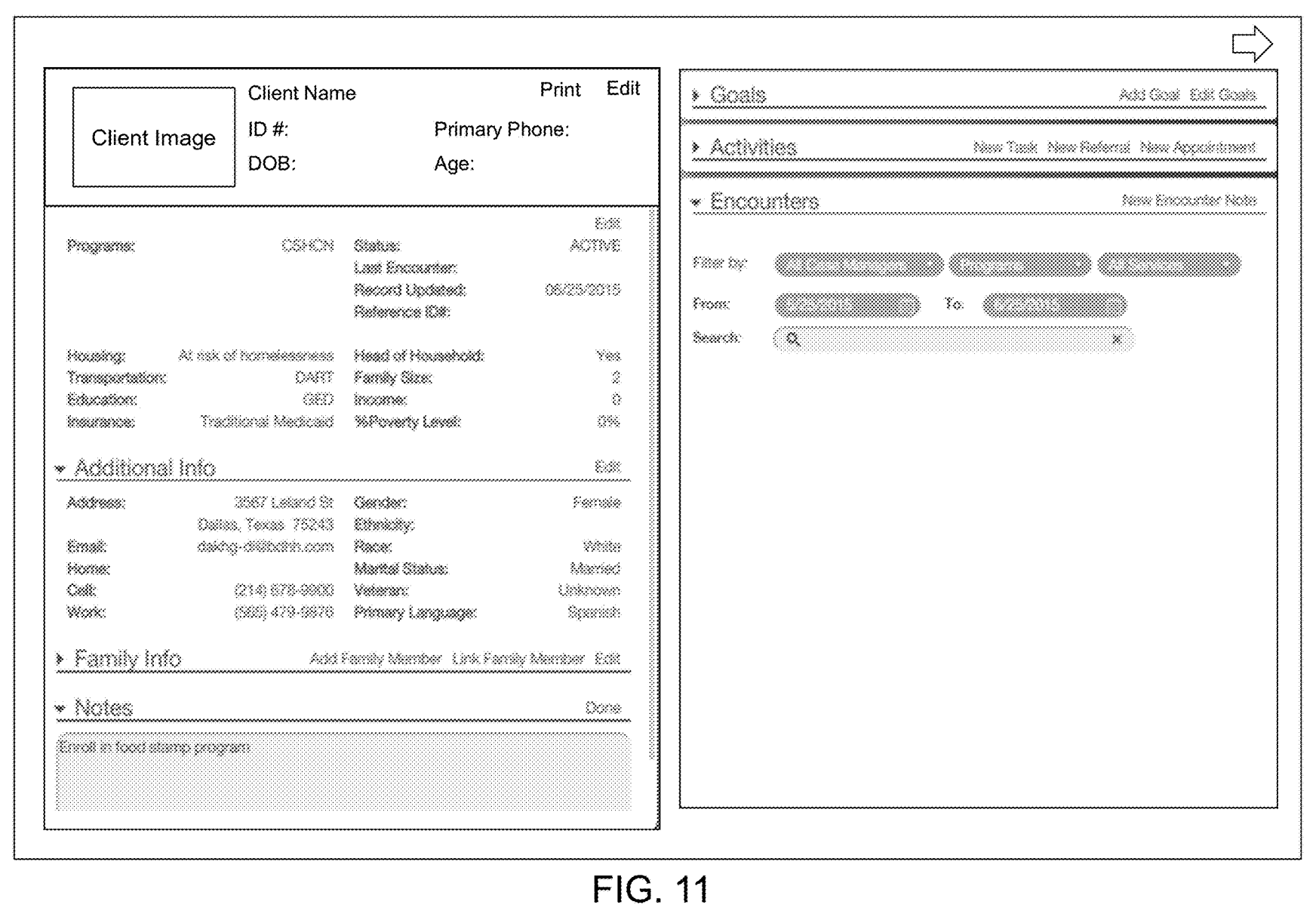

FIG. 11 is an exemplary screenshot showing more detailed information about a particular client, which may include basic profile data (photograph, name, date of birth, ID number, age, gender, ethnicity, marital status, language preference, contact information, etc.), status, enrolled programs, action items, and encounter notes. This screen captures all relevant information about a client so that it is provided to the case manager in an organized and easy to access manner.

Figure 12:
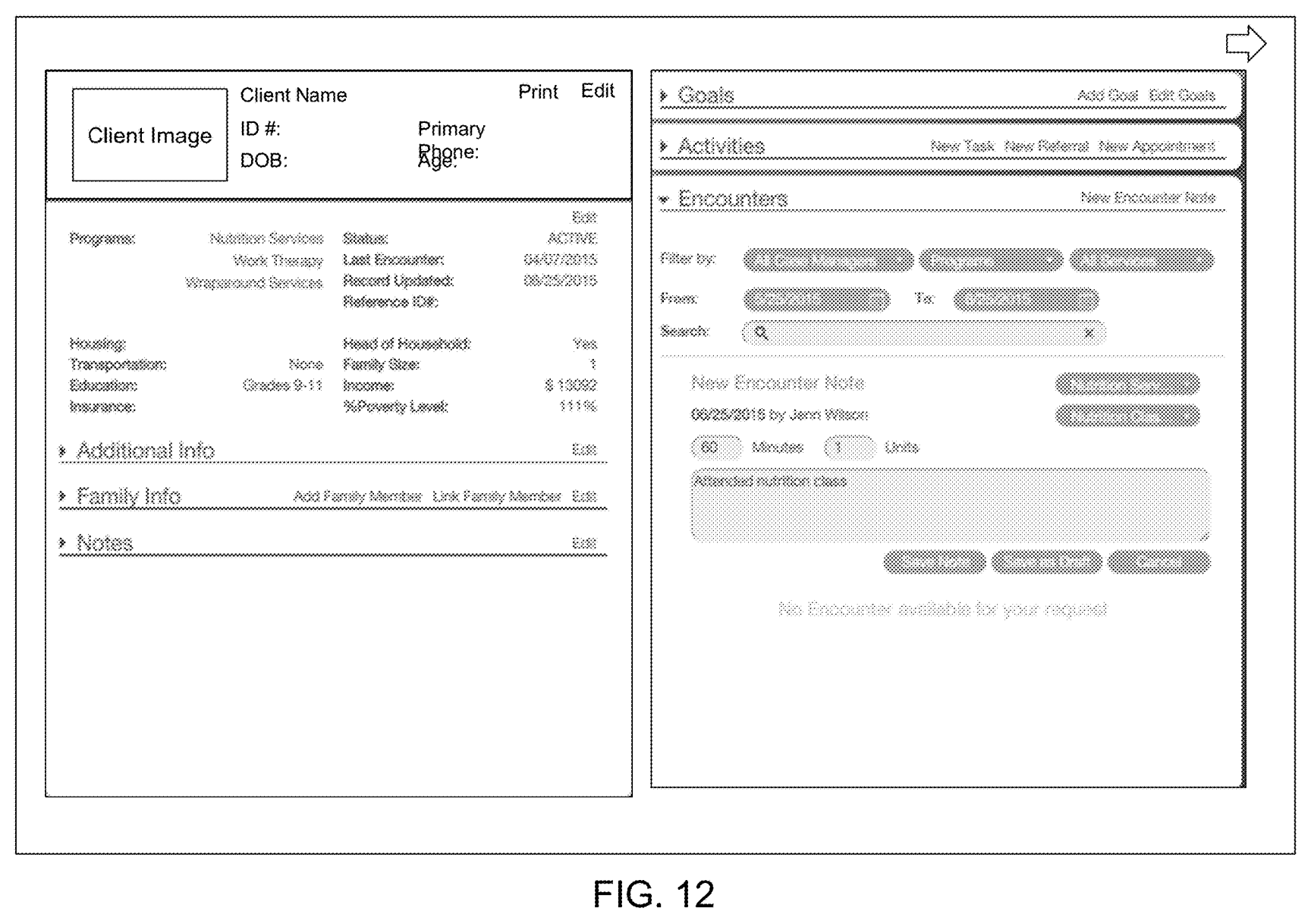
Figure 13:
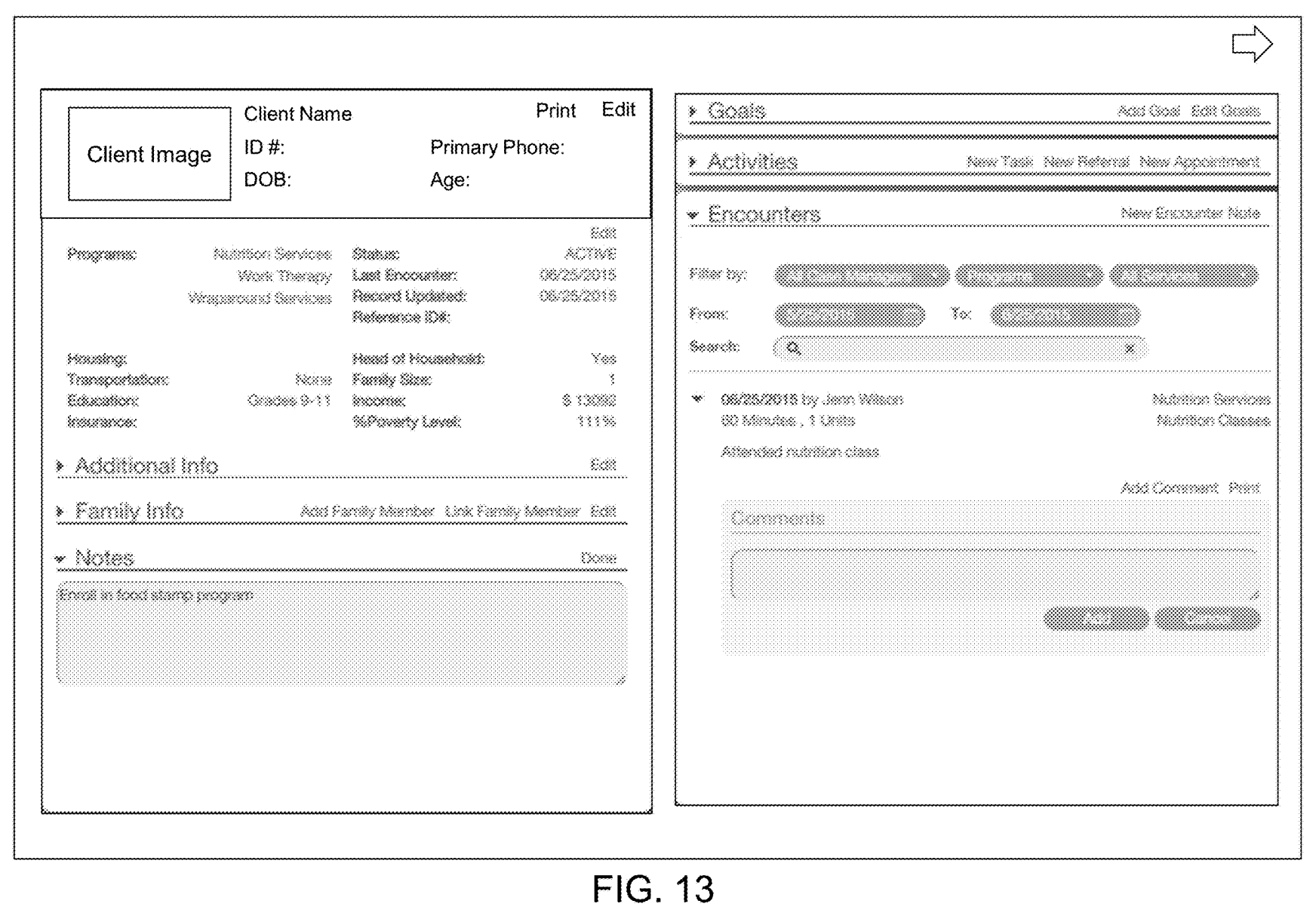
Figure 14:
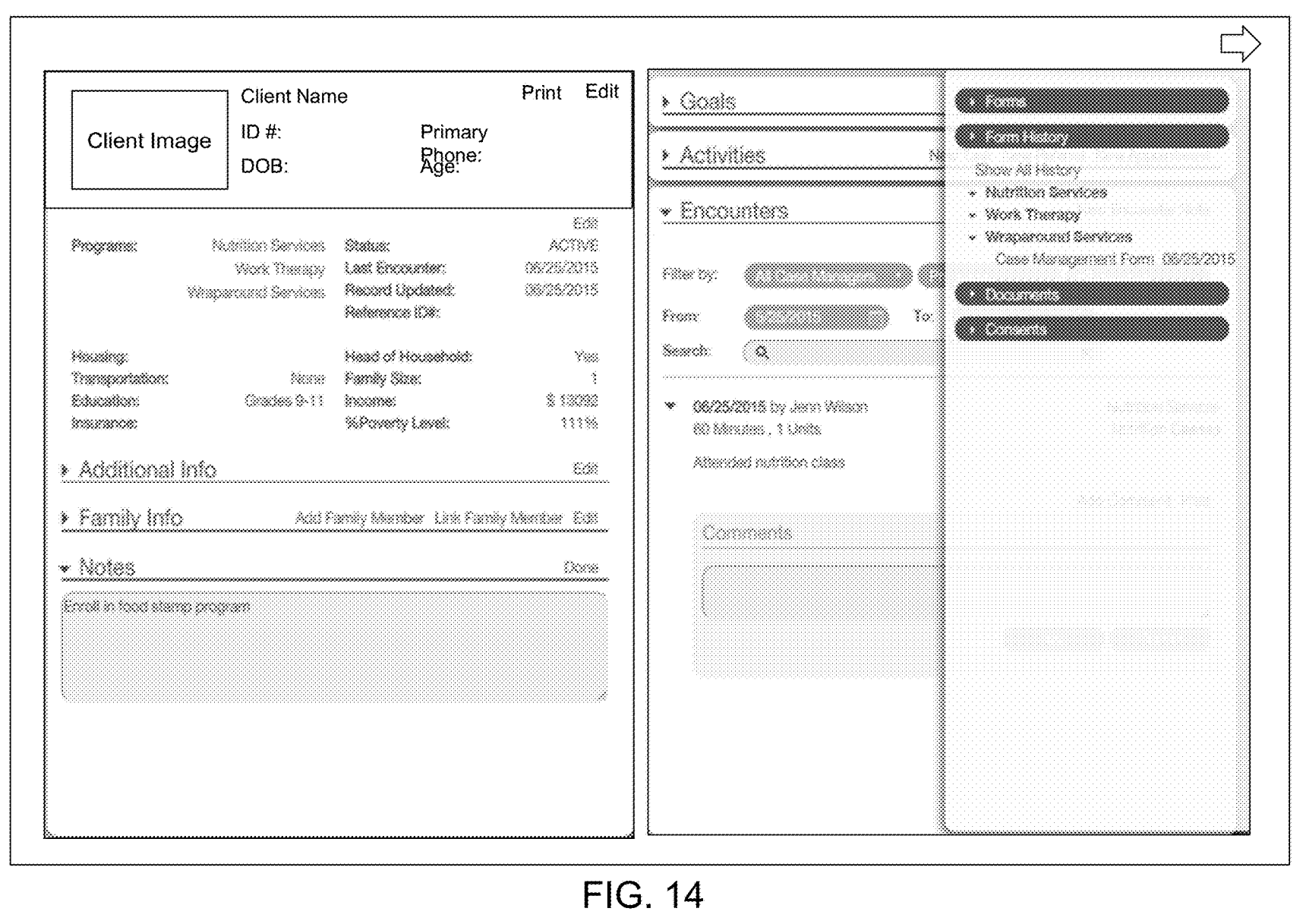

FIG. 12 is an exemplary screenshot that shows how encounter notes for a particular selected client may be entered by a case manager, for example. FIG. 13 is an exemplary screenshot that shows how comments and program/provided service notes about a particular selected client may be entered by a case manager, for example. FIG. 14 is an exemplary screenshot that shows the ability to display a virtual client document drawer and its contents by clicking on the arrow icon, for example, in the upper right corner of the screen. The virtual client document drawer facilitates easy access to documents and reference materials associated with the client, including scanned documents, signed consent forms, and other documents.

Figure 15:
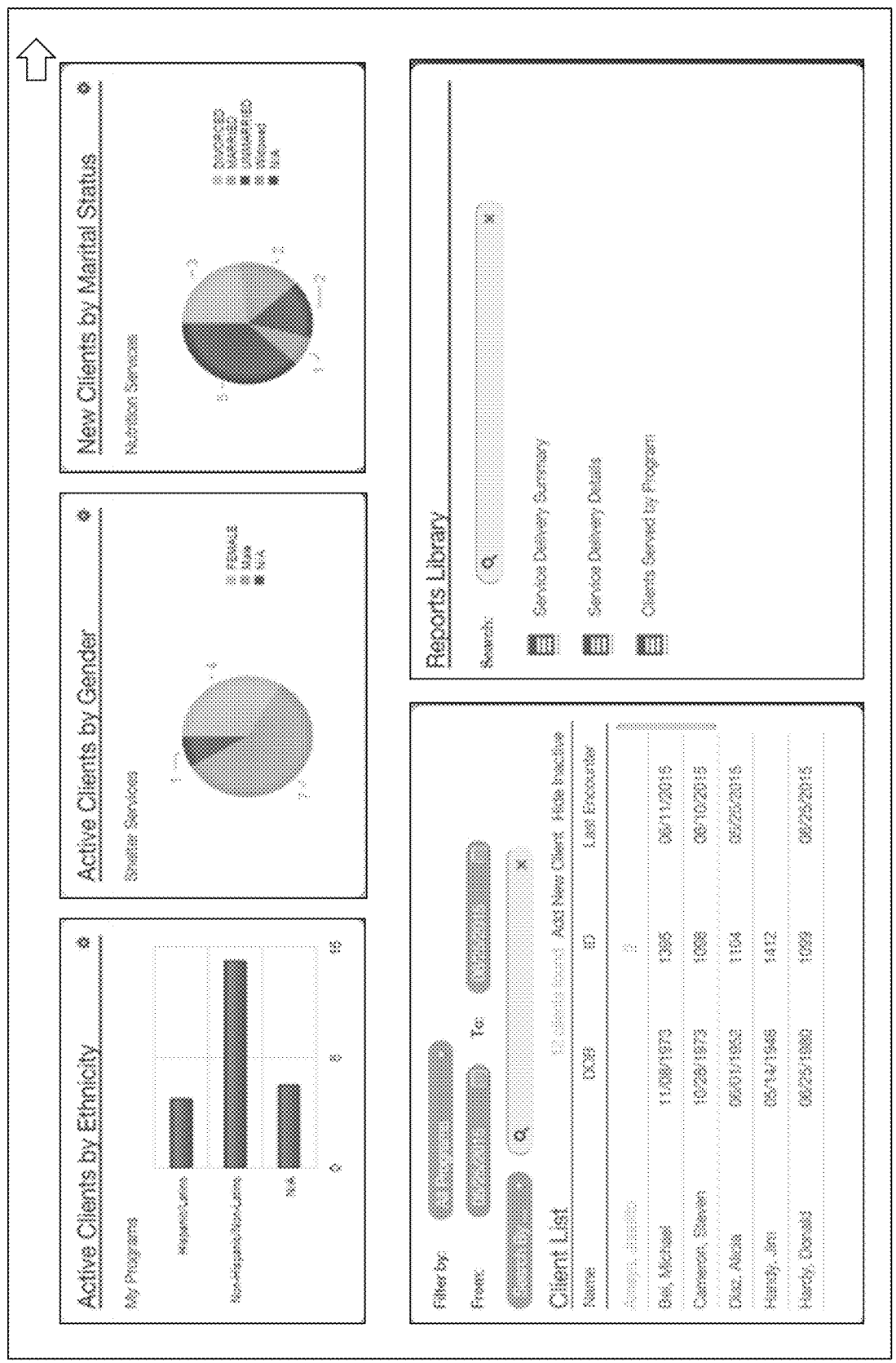
Figure 16:
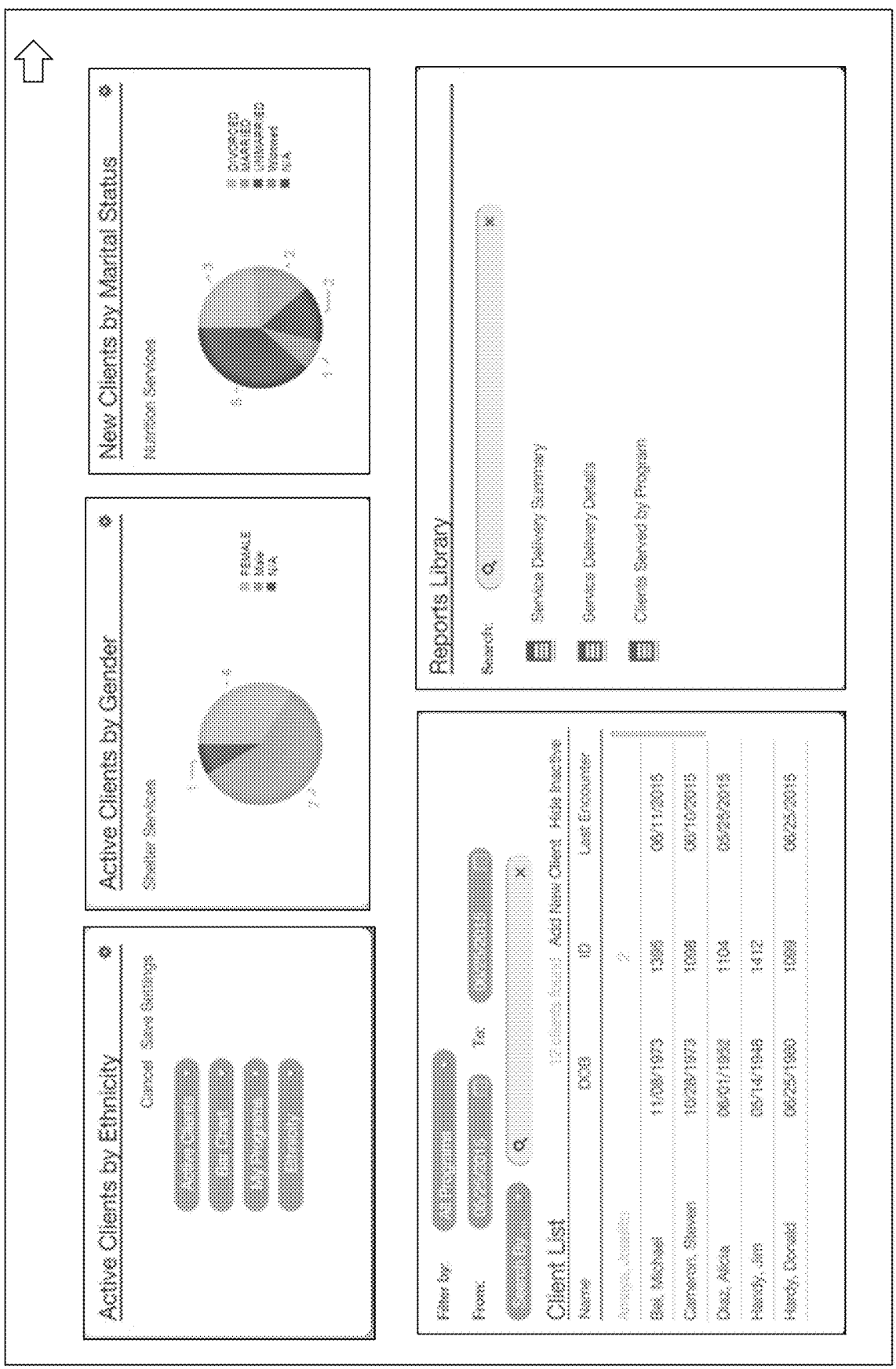

FIG. 15 is an exemplary screenshot of a program manager view that shows certain summary data about all the clients enrolled in a program or service. This exemplary screen displays three quick reports that graphically present data about clients enrolled in the program or service. For example, this screen shows a graph that provides the number of clients in a program by ethnicity, and pie charts that provide the number of clients by gender and marital status. A reports library is also displayed that provides the user's access to form and customized reports related to the program. The screen in FIG. 16 shows that data views may be configured and organized according to the user's preferences, including specifying the type of graphical representation such as bar chart, pie chart, etc. The gear icon in the upper right corner of each quick report enables the configuration of the report.

Figure 17:
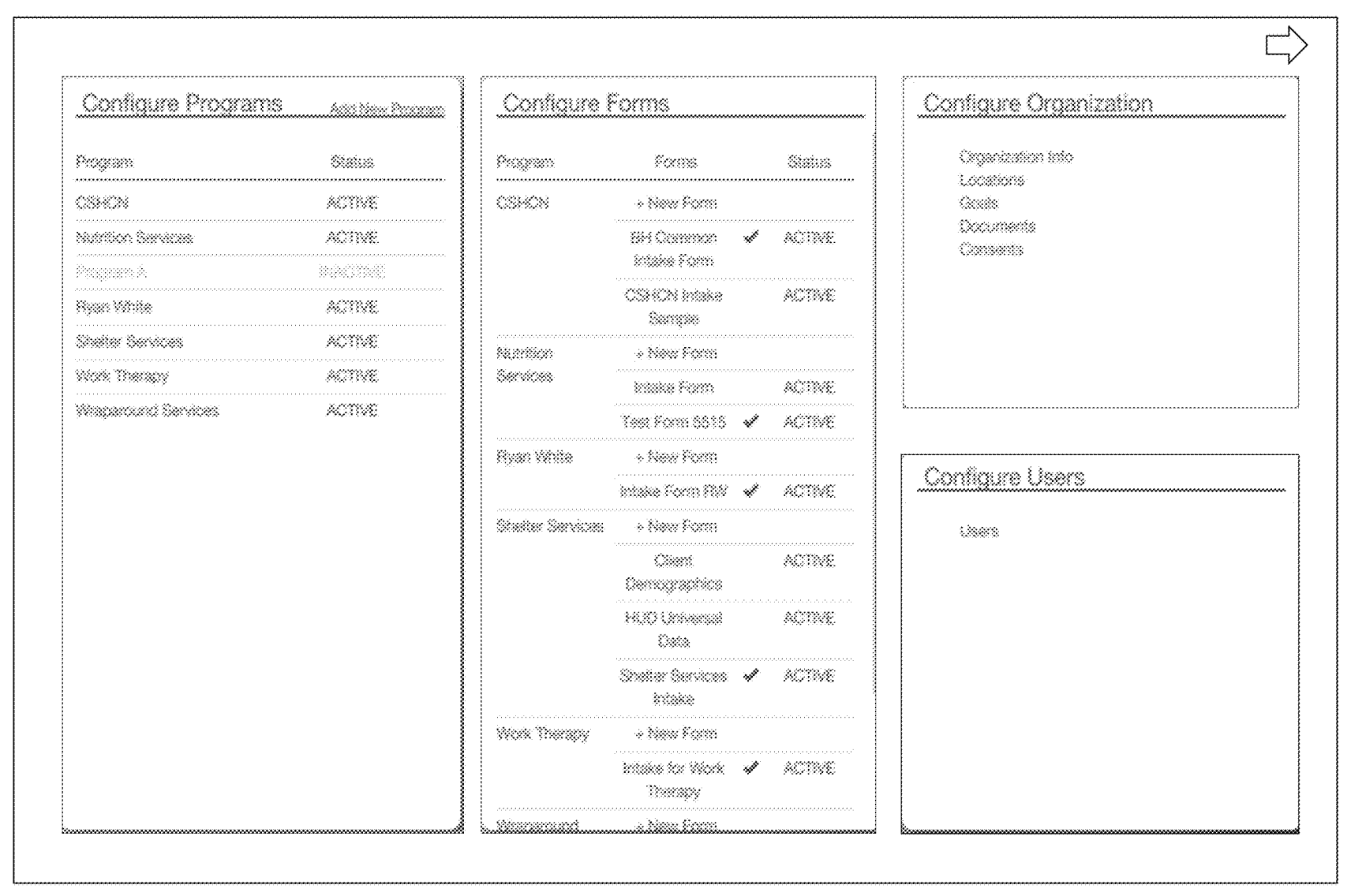
Figure 18:
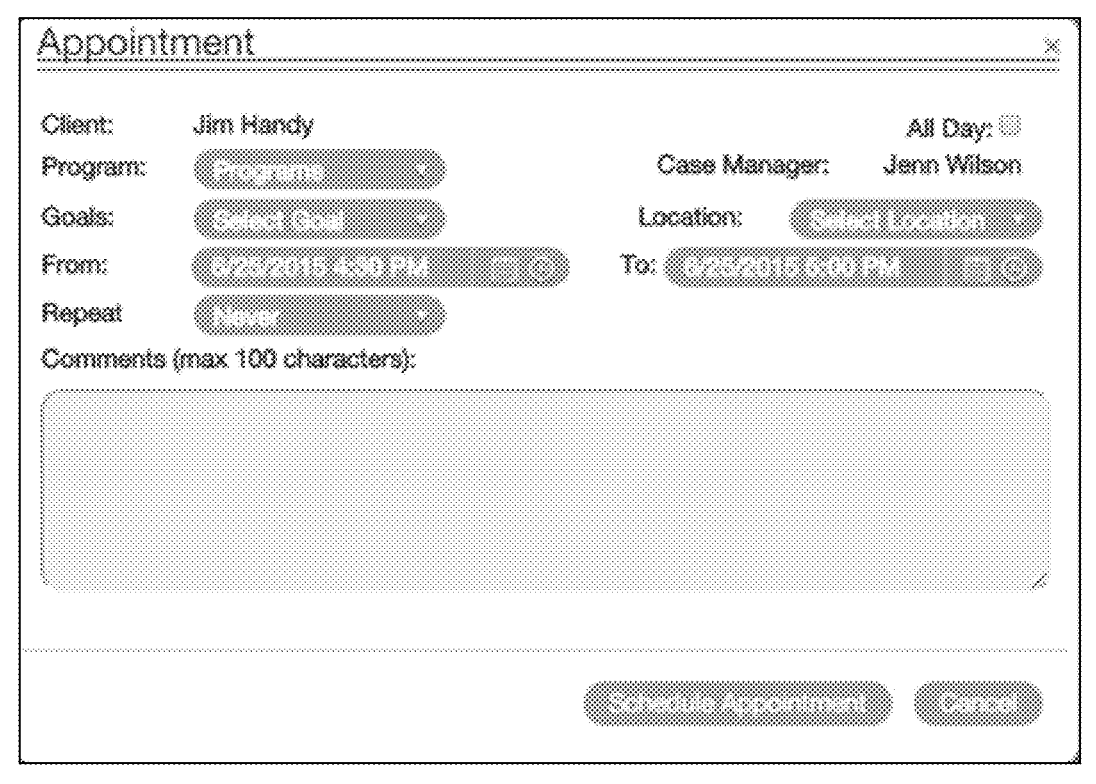
Figure 19:
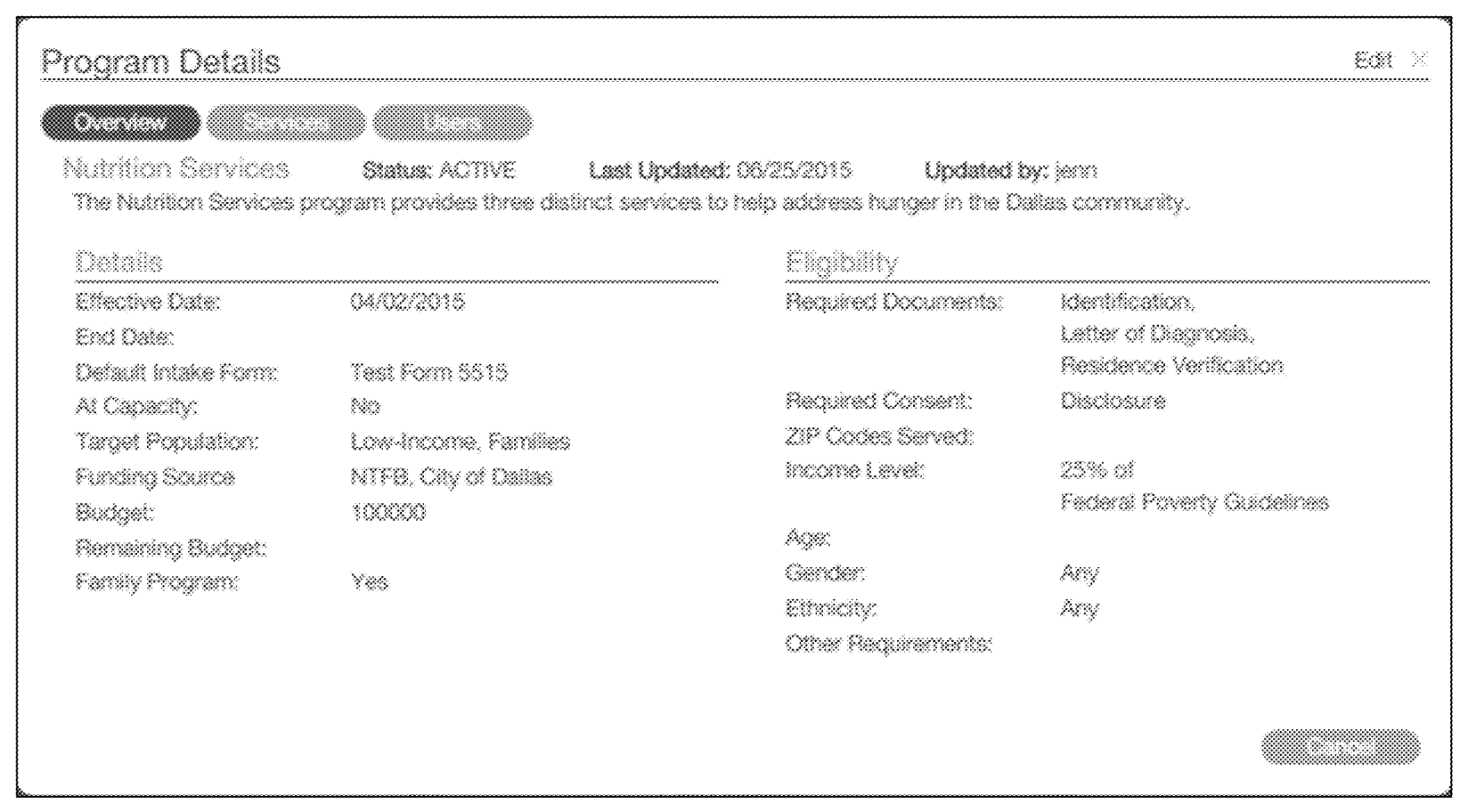
Figure 20:
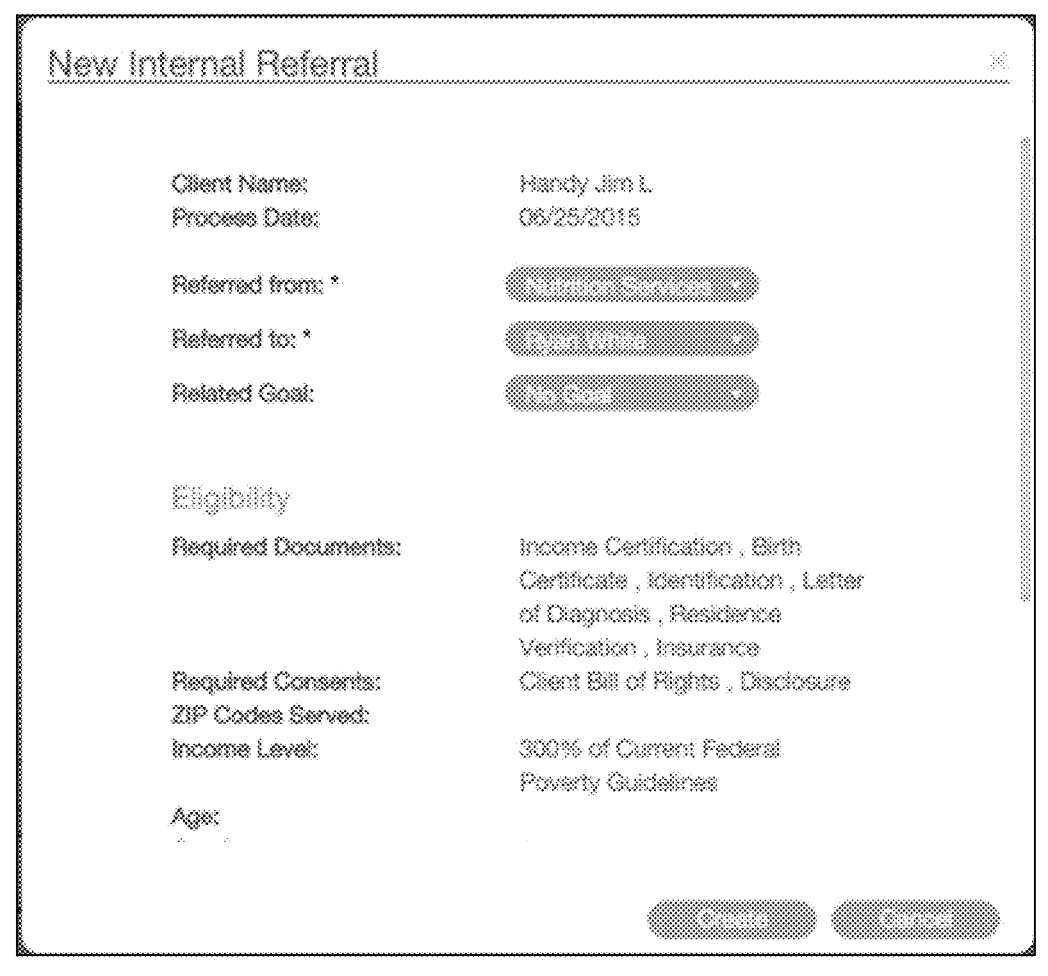

FIG. 17 shows an exemplary screen of a administrator view in which a number of parameters may be configured, including programs, forms, organizations, and users. FIG. 18 provides details of a new appointment pop-up window. FIG. 19 provides details about a particular program that the case manager or other users may access. FIG. 20 shows an internal referral window that provides information about a service or program that has been referral to a client and information associated with the referred program/service.

The system as described herein is operable to harness, simplify, sort, and present patient information in real-time or near real-time, predict and identify highest risk patients, identify adverse events, coordinate and alert practitioners, and monitor patient outcomes across time and space. The present system improves healthcare efficiency, assists with resource allocation, and presents the crucial information that lead to better patient outcomes.

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A client management tool system adapted for execution on a computer system coupled to a global computer network, comprising:
- a consent interface configured to automatically query for, receive, and organize consent and permission from the plurality of clients for data collection and analysis in compliance with laws and regulations;
- a gateway module configured to provide access to a data store storing data associated with a plurality of clients including clinical and non-clinical data;
- a collection of computerized question forms configured to obtain additional data about a client;
- a social data model defining a structure to store and organize the client data;
- at least one predictive model including a plurality of weighted variables and thresholds in consideration of the client data to identify clinical and non-clinical needs of the client and a valuation of services to address the clinical and non-clinical client needs;
- a knowledgebase of available programs and service providers able to deliver the needed services;
- a client management toolkit configured to provide recommended a course of action in response to the identified clinical and non-clinical client need, valuation, and available programs and services providers;
- calendaring appointments for scheduled services associated with the recommend program or services; and
- a data presentation module operable to present notifications, alerts, and outcome report related to service delivery of the scheduled services to the client.

2. The system of claim 1, wherein the clinical data are selected from at least one member of the group consisting of: vital signs and other physiological data; data associated with physical exams by a physician, nurse, or allied health professional; medical history; allergy and adverse medical reactions; family medical information; prior surgical information; emergency room records; medication administration records; culture results; dictated clinical notes and records; gynecological and obstetric information; mental status examination; vaccination records; radiological imaging exams; invasive visualization procedures; psychiatric treatment information; prior histological specimens; laboratory data; genetic information; physician's and nurses' notes; networked devices and monitors; pharmaceutical and supplement intake information; and focused genotype testing.

3. The system of claim 1, wherein the non-clinical data are selected from at least one member of the group consisting of: social, behavioral, lifestyle, and economic data; type and nature of employment data; job history data; medical insurance information; hospital utilization patterns; exercise information; addictive substance use data; occupational chemical exposure records; frequency of physician or health system contact logs; location and frequency of habitation change data; predictive screening health questionnaires; personality tests; census and demographic data; neighborhood environment data; dietary data; participation in food, housing, and utilities assistance registries; gender; marital status; education data; proximity and number of family or care-giving assistant data; address data; housing status data; social media data; educational level data; and data entered by clients.

4. The system of claim 1, wherein the collection of computerized question forms comprises at least one intake form.

5. The system of claim 1, wherein the collection of computerized question forms comprises at least one client assessment form.

6. The system of claim 1, wherein the predictive model uses artificial intelligence to quantify a degree of difficulty associated with a program recommended for a client and determine a relative value unit score.

7. The system of claim 1, wherein the predictive model considers a client's health conditions and social and environmental factors to quantify a degree of difficulty associated with services needed by a client and determine a relative value unit score.

8. A client management tool method, comprising:
- receiving and storing data associated with a plurality of clients including clinical and non-clinical data;
- presenting a questionnaire form including a plurality of questions, and receiving answers in response to the plurality of questions in the questionnaire;
- storing and organizing the received client data in a data store according to a social data model;
- presenting a query for, receive, and organize consent and permission from the plurality of clients for data collection and analysis in compliance with laws and regulations;
- identifying clinical and non-clinical needs of the client and determining a value score of services to address the clinical and non-clinical client needs;
- making a recommendation of course of action and needed services according to the clinical and non-clinical client needs;
- determining and displaying available programs and services providers able to deliver the needed services;
- making a referral recommendation to an available program or service according to the clinical and non-clinical client needs;
- presenting and displaying notification and/or information of the referral recommendation;
- calendaring appointments for the recommend program or service; and
- monitoring and reporting on progress and outcome of service delivery to the client.

9. The method of claim 8, wherein receiving and storing data comprises receiving and storing clinical data are selected from at least one member of the group consisting of: vital signs and other physiological data; data associated with physical exams by a physician, nurse, or allied health professional; medical history; allergy and adverse medical reactions; family medical information; prior surgical information; emergency room records; medication administration records; culture results; dictated clinical notes and records; gynecological and obstetric information; mental status examination; vaccination records; radiological imaging exams; invasive visualization procedures; psychiatric treatment information; prior histological specimens; laboratory data; genetic information; physician's and nurses' notes; networked devices and monitors; pharmaceutical and supplement intake information; and focused genotype testing.

10. The method of claim 8, wherein receiving and storing data comprises receiving and storing non-clinical data are selected from at least one member of the group consisting of: social, behavioral, lifestyle, and economic data; type and nature of employment data; job history data; medical insurance information; hospital utilization patterns; exercise information; addictive substance use data; occupational chemical exposure records; frequency of physician or health system contact logs; location and frequency of habitation change data; predictive screening health questionnaires; personality tests; census and demographic data; neighborhood environment data; dietary data; participation in food, housing, and utilities assistance registries; gender; marital status; education data; proximity and number of family or care-giving assistant data; address data; housing status data; social media data; educational level data; and data entered by clients.

11. The method of claim 8, wherein presenting a questionnaire form comprises presenting an intake form.

12. The method of claim 8, wherein presenting a questionnaire form comprises presenting a client assessment form.

13. The method of claim 8, wherein identifying needs of the client and determining a value score of services comprises using artificial intelligence to quantify a degree of difficulty associated with a program recommended for a client and determine a relative value unit score.

14. The method of claim 8, wherein identifying needs of the client and determining a value score of services comprises considering a client's health conditions and social and environmental factors to quantify a degree of difficulty associated with services needed by a client and determine a relative value unit score.

15. A client management method comprising:
displaying a list of clients enrolled in a social program;
displaying an appointment calendar showing scheduled appointments in the social program for the clients;
querying for, receiving, and organizing consent and permission for data collection and analysis from the clients;
displaying an intake questionnaire form including a plurality of questions, and receiving answers related to a client in response to the plurality of questions in the questionnaire;
storing the answers in a structured database;
displaying the answers related to the client in an organized manner;
accessing clinical and non-clinical data associated with the client;
identifying needs of the client and determining a value score of services to address the client needs based on the clinical and non-clinical data and the answers to the questions;
making a recommendation of course of action and needed services according to the client needs;
querying a database, determining and displaying recommended programs and services providers able to deliver the needed services;
making a referral to the recommended program or service according to the client needs;
scheduling the recommended program or service for the client;
calendaring appointments for scheduled services associated with the recommend program or services; and
generating an outcome report associated with the scheduled program or services.

16. The method of claim 15, further comprising:
presenting and displaying notification and/or information of the recommendation; and
monitoring progress of service delivery to the client.

17. The method of claim 15, further comprising displaying an assessment questionnaire form including a plurality of questions, and receiving answers related to a client in response to the plurality of questions in the assessment questionnaire.

18. The method of claim 15, further comprising displaying data associated with clients enrolled in a particular program.

19. The method of claim 15, wherein identifying needs of the client and determining a value score of services comprises using artificial intelligence to quantify a degree of difficulty associated with a program recommended for a client and determine a relative value unit score.

20. The method of claim 15, wherein identifying needs of the client and determining a value score of services comprises considering a client's health conditions and social and environmental factors to quantify a degree of difficulty associated with services needed by a client and determine a relative value unit score.

\* \* \* \* \*